(12) United States Patent
Ohba et al.

(10) Patent No.: US 7,589,166 B2
(45) Date of Patent: Sep. 15, 2009

(54) THIOPHENE-CONTAINING COMPOUND AND POLYMER THEREOF

(75) Inventors: Yoshihiro Ohba, Yonezawa (JP); Kazuaki Sato, Yonezawa (JP); Yohei Nishino, Minamiashigara (JP); Mieko Seki, Minamiashigara (JP); Takeshi Agata, Minamiashigara (JP); Kiyokazu Mashimo, Minamiashigara (JP); Katsuhiro Sato, Minamiashigara (JP); Hirohito Yoneyama, Minamiashigara (JP); Daisuke Okuda, Minamiashigara (JP); Hidekazu Hirose, Minamiashigara (JP); Toru Ishii, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 608 days.

(21) Appl. No.: 11/404,991

(22) Filed: Apr. 14, 2006

(65) Prior Publication Data
US 2006/0293500 A1 Dec. 28, 2006

(30) Foreign Application Priority Data
Jun. 27, 2005 (JP) .............................. 2005-187486
Apr. 11, 2006 (JP) .............................. 2006-109153

(51) Int. Cl.
C08G 75/00 (2006.01)

(52) U.S. Cl. ........................................ 528/377; 549/59

(58) Field of Classification Search ................. 528/377
See application file for complete search history.

(56) References Cited

U.S. PATENT DOCUMENTS

| 4,801,517 | A | 1/1989 | Frechet et al. |
| 4,806,443 | A | 2/1989 | Yanus et al. |
| 4,806,444 | A | 2/1989 | Yanus et al. |
| 4,937,165 | A | 6/1990 | Ong et al. |
| 4,959,228 | A | 9/1990 | Skrgatic et al. |
| 4,983,482 | A | 1/1991 | Ong et al. |
| 5,034,296 | A | 7/1991 | Ong et al. |
| 5,817,739 | A * | 10/1998 | Nukada et al. .............. 528/292 |

FOREIGN PATENT DOCUMENTS

| JP | 59-28903 | 7/1984 |
| JP | 61-20953 | 1/1986 |
| JP | 1-134456 | 5/1989 |
| JP | 1-134457 | 5/1989 |
| JP | 1-134462 | 5/1989 |
| JP | 1-134465 | 5/1989 |
| JP | 4-133065 | 5/1992 |
| JP | 4-133066 | 5/1992 |

OTHER PUBLICATIONS

Proceedings of the 37th Applied Physics Joint Meeting 31p-K-12, 1990.
Nature, vol. 357, 477, 1992.
Proceedings of the 42nd Polymer Forum 20J21, 1993.

* cited by examiner

Primary Examiner—Randy Gulakowski
Assistant Examiner—Shane Fang
(74) Attorney, Agent, or Firm—Fildes & Outland, P.C.

(57) ABSTRACT

The present invention provides a thiophene-containing compound represented by Formula (I) and a thiophene-containing compound polymer using the thiophene-containing compound. In Formula (I), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_5$ each independently represent a hydrogen atom, an alkyl group, a cyano group, a halogen group, a substituted amino group, a substituted or unsubstituted aryl group, or a substituted or unsubstituted aralkyl group; 1 represents an integer from 1 to 5; and m and k each independently represent 0 or 1.

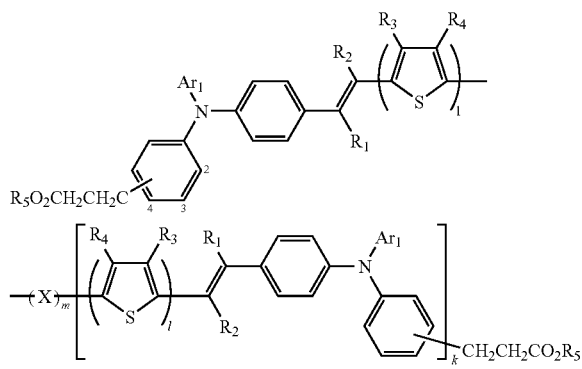

Formula (I)

18 Claims, 3 Drawing Sheets

THIOPHENE-CONTAINING COMPOUND AND POLYMER THEREOF

CROSS-REFERENCE TO RELATED APPLICATION

This application claims priority under 35 USC 119 from Japanese Patent Application Nos. 2005-187486 and 2006-109153, the disclosures of which are incorporated by reference herein.

BACKGROUND OF THE INVENTION

1. Field of the Invention

The present invention relates to a thiophene-containing compound and a polymer thereof useful as materials for organic electronic devices such as electrophotographic photoreceptors, organic electroluminescent devices and organic transistors. Specifically, the invention relates to a thiophene-containing compound and a polymer thereof superior in charge-transporting characteristics and light-emitting characteristics.

2. Description of the Related Art

As charge-transporting materials, charge-transporting polymers, a typical example of which is polyvinylcarbazole (PVK), and low molecular weight compound dispersed systems, in which a charge-transporting low molecular weight compound is dispersed in a polymer, are well known. Low molecular weight dispersed systems are mainly used, particularly for electrophotographic photoreceptors since the systems are variable in raw material thereof and high function can be obtained easily.

In recent years, electrophotographic photoreceptors have been used in high-speed copiers or printers as the performance of organic photoreceptors has become more advanced. However, the performance is not necessarily sufficient at present, and a longer life span thereof is earnestly required. As for the current mainstream charge-transporting layer of low molecular weight systems, the electric properties thereof are becoming sufficiently satisfactory. However, the charge-transporting layer has a problem in that the layer is essentially poor in mechanical strength and is weak against abrasion since a low molecular weight compound is dispersed in a polymer.

In organic electroluminescent devices, low molecular weight charge-transporting materials are generally used by vapor-deposition. However, since organic electroluminescent devices are driven with high current density, i.e. some mA/cm$^2$, a huge amount of Joule heat is generated, whereby morphologic changes can easily occur, leading to phenomenon such as decrease in brilliance and dielectric breakdown. As a result, the life span of devices is shortened. As for high molecular weight charge-transporting materials, there are not so many materials having both charge-transporting properties and light emitting properties, and therefore, using such materials has been problematic in view of efficiency and life span of devices.

On the other hand, charge-transporting polymers, a typical example of which is PVK, are actively researched at present as a photoconducting material for electrophotographic photoreceptors, and also actively researched as a charge-transporting material since there is a possibility that the above-mentioned drawbacks of the polymers can be greatly overcome as described in, for example, *Proceedings of the 37$^{th}$ Applied Physics Joint Meeting* 31p-K-12, 1990, the disclosure of which is incorporated by reference herein. For example, U.S. Pat. No. 4,806,443 discloses a polycarbonate obtained by polymerizing a specific dihydroxyarylamine and bischloroformate, and U.S. Pat. No. 4,806,444 discloses a polycarbonate obtained by polymerizing a specific dihydroxyarylamine and phosgene (the disclosures of U.S. Pat. Nos. 4,806,443 and 4,806,444 are incorporated by reference herein).

Moreover, U.S. Pat. No. 4,801,517, the disclosure of which is incorporated by reference herein, discloses a polycarbonate obtained by polymerizing bishydroxyalkylarylamine, and bischloroformate or phosgene, and U.S. Pat. Nos. 4,937,165 and 4,959,228, the disclosures of which are incorporated by reference herein, disclose a polycarbonate obtained by polymerizing a specific dihydroxyarylamine or bishydroxyalkylarylamine, bishydroxyalkylamine, and bischloroformate, or a polyester obtained by polymerizing the amine and bisacylhalide. Furthermore, U.S. Pat. No. 5,034,296, the disclosure of which is incorporated by reference herein, discloses a polyester, or a polycarbonate of an arylamine having a specific fluorene skeleton, and U.S. Pat. No. 4,983,482, the disclosure of which is incorporated by reference herein, discloses a polyurethane. Additionally, Japanese Patent Application Publication (JP-B) No. 59-28903, the disclosure of which is incorporated by reference herein, discloses a polyester having, as a main chain, a specific bisstyrylbisarylamine.

Japanese Patent Application Laid-Open (JP-A) Nos. 61-20953, 1-134456, 1-134457, 1-134462, 4-133065 and 4-133066, the disclosures of which are incorporated by reference herein, suggest polymers and photoreceptors having, as a pendant, a charge-transporting substituent such as hydrazone and triarylamine.

Organic electroluminescent devices using π-conjugated polymers represented by paraphenylenevinylene (PPV) (see, for example, *Nature*, Vol. 357, 477, 1992, the disclosure of which is incorporated by reference herein), and organic electroluminescent devices using polymers having triphenylamine introduced into the side chain of polyphosphazene are proposed (see, for example, *Proceedings of the 42$^{nd}$ Polymer Forum* 20J21, 1993, the disclosure of which is incorporated by reference herein).

Various properties such as solubility, film-formability, mobility, heat resistance, and matching of oxidation potential are required of charge-transporting materials. In order to satisfy these requirements, generally a substituent is introduced to the polymer so as to control the physical properties thereof.

Since the physical properties of the charge-transporting polymer have high correlation with the physical properties of a charge-transporting monomer, which is a raw material of the polymer, the molecular design of the charge-transporting monomer (low molecular weight material) becomes important.

The monomer which is the raw material of the above-mentioned triarylamine polymer can be roughly classified into two kinds, that is, (1) dihydroxyarylamine, and (2) bishydroxyalkylarylamine.

However, since dihydroxyarylamine of (1) has an aminophenolic structure, it is easily oxidized and is not easily purified. Particularly in a case in which dihydroxyarylamine has the hydroxy group at para position, the dihydroxyarylamine becomes more unstable. Additionally, dihydroxyarylamine has a structure in which oxygen of the substituent bonds directly to the aromatic ring; therefore, charge distribution is easily unbalanced by the electron-withdrawing property of the oxygen. As a result, a problem occurs in that the mobility thereof falls easily.

On the other hand, bishydroxyalkylarylamine of (2) is not affected strongly by the electron-withdrawing property of oxygen because of the methylene group, but monomer is not easily synthesized. That is, according to a reaction of diarylamine or diarylbenzidine with 3-bromoiodobenzene, a mixture tends to be produced since both bromine and iodine have reactivity. Thus, the yield of the target amine falls. The following problem also arises: alkyllithium, which is used when lithium is bonded to a bromine, or ethylene oxide is highly dangerous and toxic and therefore requires careful handling.

The π-conjugated polymers represented by PPV described above, and the organic electroluminescent devices having triphenylamine introduced into the polyphosphazene side chain involve problems in color tone, luminous intensity and durability.

Thus, there is a need for development of an organic electronic material which can be synthesized easily, exhibits excellent charge-transporting performance and is superior in light-emitting characteristics, in order to develop organic electronic devices, such as organic electroluminescent devices, that have greater luminescence brightness and are superior in stability during repeated use.

SUMMARY OF THE INVENTION

The present invention has been made in view of the above circumstances and provides a new compound and a new polymer. That is, the invention provides a thiophene-containing compound and a polymer thereof.

According to an aspect of the invention, a thiophene-containing compound represented by Formula (I) is provided.

Formula (I)

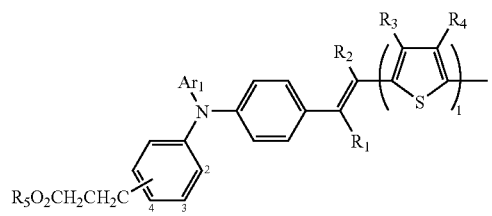

-continued

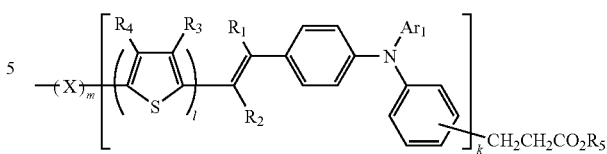

In Formula (I), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_5$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

According to another aspect of the invention, a thiophene-containing compound polymer represented by Formula (III-1) or (III-2) is provided.

Formula (III-1)

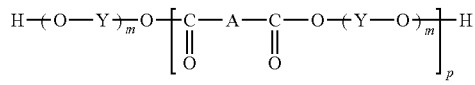

Formula (III-2)

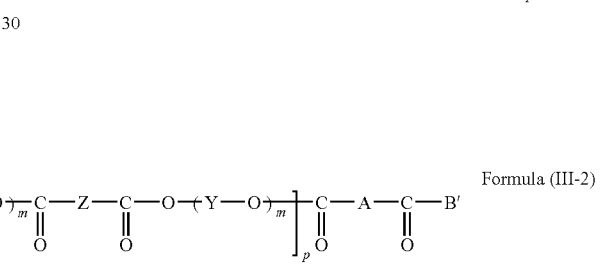

In Formulae (III-1) and (III-2), Y represents a divalent hydrocarbon group; Z represents a divalent hydrocarbon group; B and B' each independently represent —O—(Y—O)$_m$—H or —O—(Y—O)$_m$—CO-Z-CO—OR$_7$; $R_7$ represents a hydrogen atom, an alkyl group, a substituted or unsubstituted aryl group, a substituted or unsubstituted aralkyl group; m represents an integer from 1 to 5; p represents an integer from 5 to 5,000; and A represents a group represented by Formula (IV).

Formula (IV)

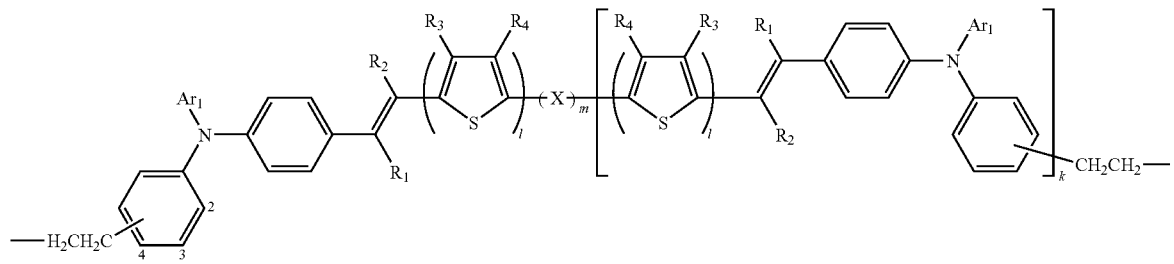

In Formula (IV), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_4$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

DETAILED DESCRIPTION OF THE INVENTION

Figure 1A:
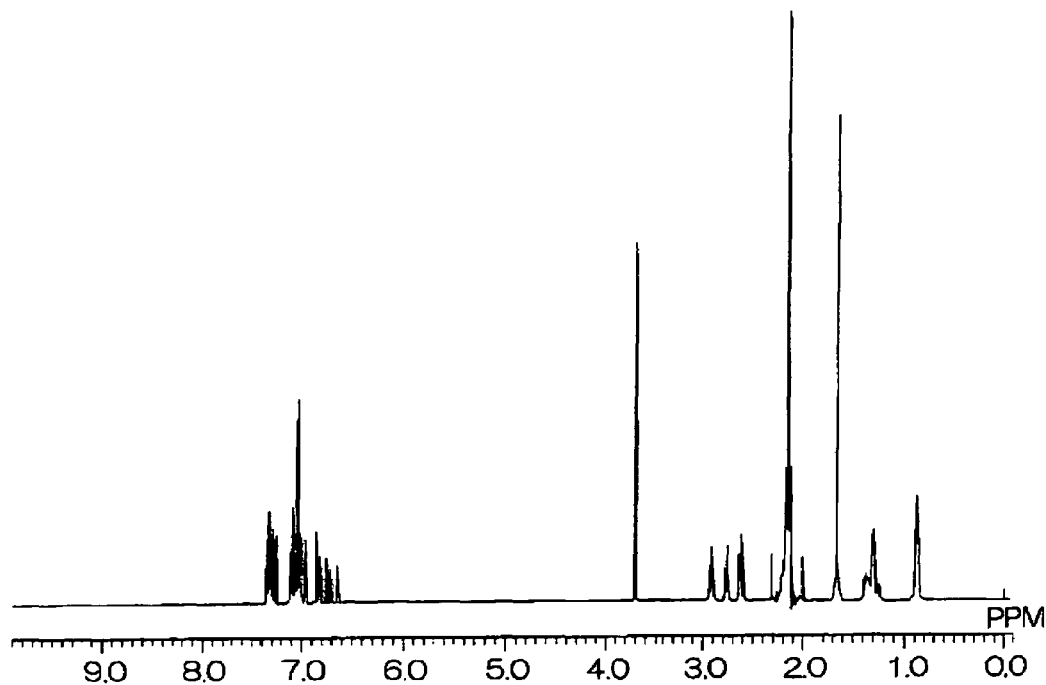
FIGS. 1A and 1B show measurement results, respectively NMR and IR spectra, of compound 2.

A thiophene-containing compound according to the present invention is represented by Formula (I), and a polymer thereof is represented by Formulae (III-1) or (III-2).

The thiophene-containing compound and the polymer thereof have superior electric charge-transporting property, solubility, and film-forming property, and have superior charge-transporting characteristics and light-emitting characteristics. In addition, the thiophene-containing compound and the polymer thereof according to the invention are easily synthesized, and it is possible to control their physical properties such as ionization potential (IP), glass transition temperature (Tg), and emission wavelength by introducing a substituent group thereto. Thus, the thiophene-containing compound and the polymer thereof according to the invention are very useful materials for organic electronic devices such as organic photoreceptors, organic electroluminescent devices, and organic transistors.

Formula (I)

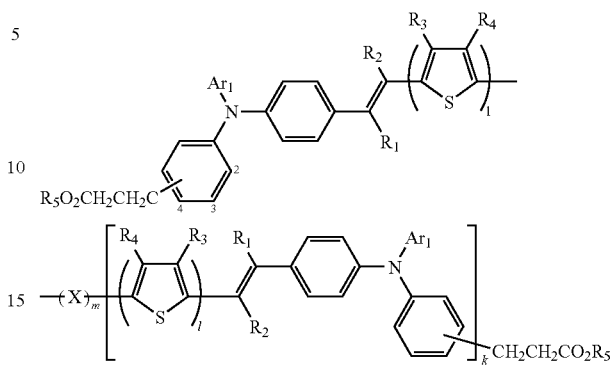

In Formula (I), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_5$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

Formula (III-1)

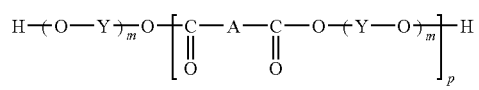

Formula (III-2)

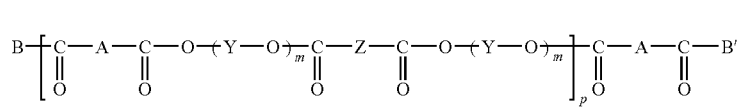

In Formulae (III-1) and (III-2), Y represents a divalent hydrocarbon group; Z represents a divalent hydrocarbon group; B and B' each independently represent —O—(Y—O)$_m$—H or —O—(Y—O)$_m$—CO- Z-CO—OR$_7$; $R_7$ represents a hydrogen atom, an alkyl group, a substituted or unsubstituted aryl group, a substituted or unsubstituted aralkyl group; m represents an integer from 1 to 5; p represents an integer from 5 to 5,000; and A represents a group represented by Formula (IV).

Formula (IV)

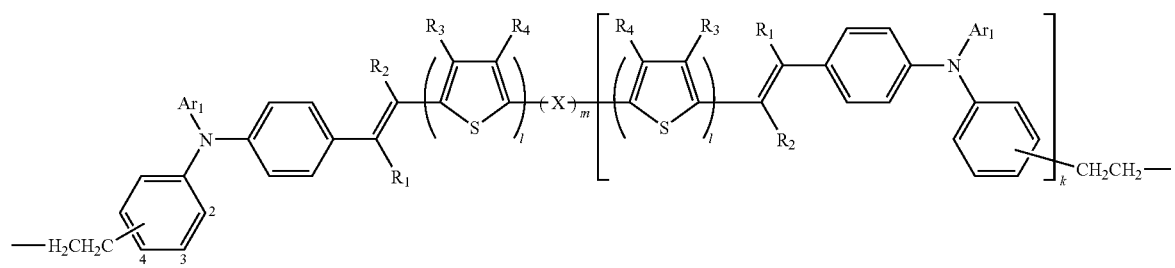

In Formula (IV), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_4$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

Specific examples of $Ar_1$ and X in Formulae (I) and (IV) will be described. In Formulae (I) and (IV), $Ar_1$ represents a substituted or unsubstituted monovalent aromatic group, specifically, a substituted or unsubstituted phenyl group, a substituted or unsubstituted monovalent polynuclear aromatic hydrocarbon having 2 to 20 aromatic rings, a substituted or unsubstituted monovalent condensed aromatic hydrocarbon having 2 to 20 aromatic rings, a substituted or unsubstituted monovalent aromatic heterocyclic ring, or a substituted or unsubstituted monovalent aromatic group containing at least one aromatic heterocyclic ring, although the number of the aromatic or heterocyclic rings is not particularly limited.

In the invention, the polynuclear aromatic hydrocarbon means specifically a polycyclic aromatic defined as follows. The "polynuclear aromatic hydrocarbon" represents a hydrocarbon in which two or more aromatic rings constituted of carbon and hydrogen atoms are bound to each other via a carbon-carbon bond. Specific examples thereof include biphenyl, terphenyl, stilbene and the like.

The "condensed aromatic hydrocarbon" represents a hydrocarbon having two or more aromatic rings constituted of carbon and hydrogen atoms and the two aromatic rings share a pair of adjacent carbon atoms and are bound to each other via the pair of carbon atoms. Specific examples thereof include naphthalene, anthracene, phenanthrene, pyrene, perylene, fluorene and the like.

In Formulae (I) and (IV), the aromatic heterocyclic ring selected as one of the structures representing $Ar_1$ represents an aromatic ring containing one or more elements other than carbon and hydrogen atoms. As the aromatic heterocyclic ring, those in which the number (Nr) of the atoms constituting each cyclic skeleton is 5 and/or 6 are preferably used.

The kinds and number of the atoms other than carbon (heteroatom) constituting the cyclic skeleton are not particularly limited, but, for example, a sulfur, nitrogen or oxygen atom, or the like is preferably used. Two or more kinds of and/or two or more heteroatoms may be contained in the cyclic skeleton. In particular, preferable heterocyclic rings having a five-membered cyclic structure include thiophene, thiophine, pyrrole, furan, and rings obtained by replacing a carbon atom at the third or fourth position of the above rings with a nitrogen atom; and favorable heterocyclic rings having a six-membered cyclic structure include a pyridine ring.

In Formulae (I) and (IV), the aromatic group containing an aromatic heterocyclic ring selected as one of the structures representing $Ar_1$ represents a linking group containing at least one of the aromatic heterocyclic rings described above in an atomic group forming the skeleton. Each of these may be conjugated entirely or partially, but is preferably conjugated entirely, from the point of charge-transporting property and luminous efficiency.

In Formulae (I) and (IV), examples of the substituent groups on the monovalent aromatic group represented by $Ar_1$ include a hydrogen atom, alkyl groups, alkoxy groups, a phenoxy group, aryl groups, aralkyl groups, substituted amino groups, halogen atoms and the like. The alkyl group preferably has 1 to 10 carbon atoms, and examples thereof include methyl, ethyl, propyl, and isopropyl groups and the like. The alkoxy group preferably has 1 to 10 carbon atoms, and examples thereof include methoxy, ethoxy, propoxy, and isopropoxy groups and the like. The aryl group preferably has 6 to 20 carbon atoms, and examples thereof include phenyl and toluic groups and the like. The aralkyl group preferably has 7 to 20 carbon atoms, and examples thereof include benzyl and phenethyl groups and the like. Examples of the substituent groups on the substituted amino groups include alkyl groups, aryl groups, and aralkyl groups; and specific examples thereof are the same as those described above.

In Formulae (I) and (IV), X represents a divalent straight-chain hydrocarbon group having 1 to 6 carbon atoms, a divalent branched-chain hydrocarbon group having 2 to 10 carbon atoms, or a substituted or unsubstituted divalent aromatic group; and is preferably selected from divalent straight-chain hydrocarbon groups having 2 to 6 carbon atoms, divalent branched-chain hydrocarbon groups having 3 to 7 carbon atoms, substituted or unsubstituted divalent polynuclear aromatic hydrocarbons having 1 to 8 aromatic rings, substituted or unsubstituted divalent condensed aromatic hydrocarbons having 1 to 8 aromatic rings, and substituted or unsubstituted divalent aromatic heterocyclic rings having 1 to 11 heterocyclic rings. Structures of specific examples of straight-chain hydrocarbon groups and branched-chain hydrocarbon groups are shown below, but the straight-chain hydrocarbon groups and branched-chain hydrocarbon groups are not limited thereto:

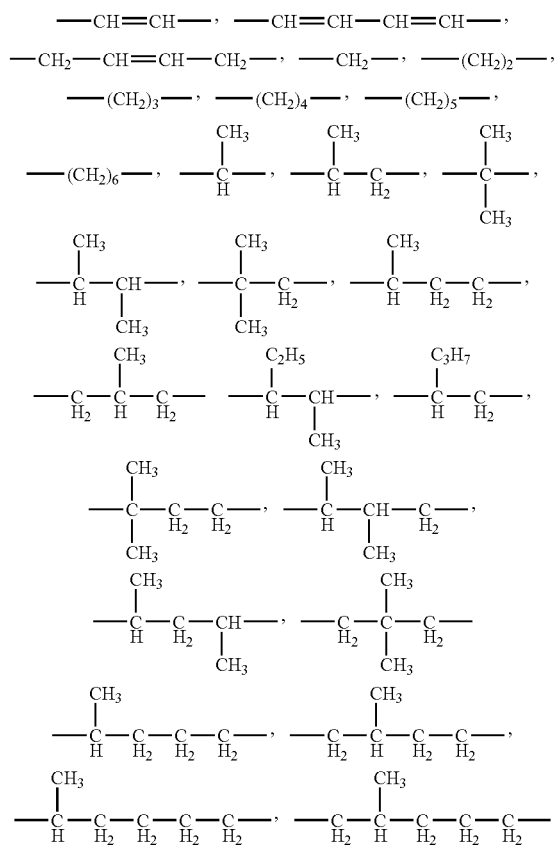

-continued

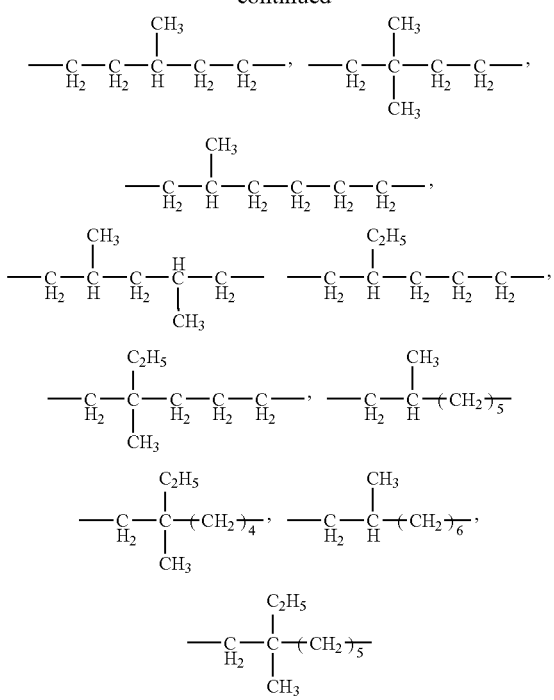

Structures of specific examples of substituted or unsubstituted divalent aromatic groups are shown in the following Structural Formulae (V-1) to (V-8), but the substituted or unsubstituted divalent aromatic groups are not limited thereto:

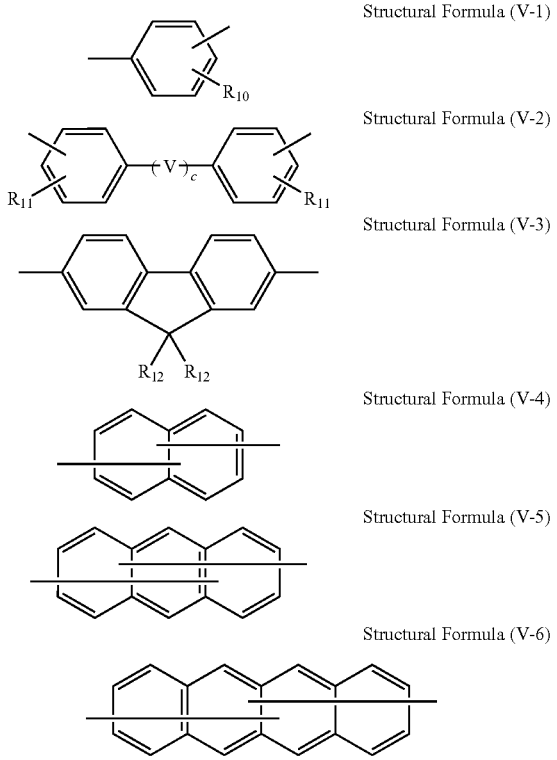

-continued

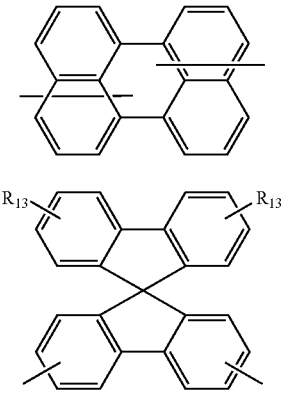

Structural Formula (V-7)

Structural Formula (V-8)

In the above formulae, $R_{10}$ to $R_{13}$ each independently represent a hydrogen atom, an alkyl group having 1 to 4 carbon atoms, an alkoxy group having 1 to 4 carbon atoms, a substituted or unsubstituted phenyl group, a substituted or unsubstituted aryl group, a substituted or unsubstituted aralkyl group, or a halogen atom; and c represents an integer of 0 or 1.

In addition, in Structural Formula (V-2), V represents a group selected from the groups represented by the following Structural Formulae (VI-1) to (VI-11):

 (VI-1)

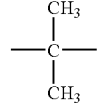 (VI-2)

 (VI-3)

 (VI-4)

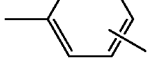 (VI-5)

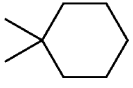 (VI-6)

 (VI-7)

 (VI-8)

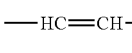 (VI-9)

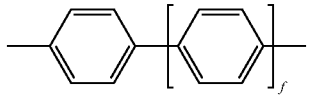 (VI-10)

-continued

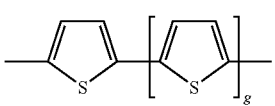
(VI-11)

In Structural Formulae (VI-1), (VI-10) and (VI-11), e represents an integer from 1 to 5; and each of f and g represents an integer from 0 to 5.

In Formulae (III-1) and (III-2), Y and Z each preferably independently represent a group selected from the groups represented by the following Structural Formulae (VII-1) to (VII-7).

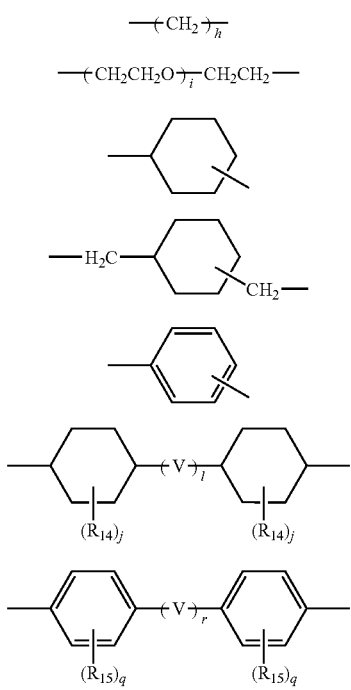

(VII-1)
(VII-2)
(VII-3)
(VII-4)
(VII-5)
(VII-6)
(VII-7)

In the above structural formulae, each of $R_{14}$ and $R_{15}$ represents a hydrogen atom, an alkyl group having 1 to 4 carbon atoms, an alkoxy group having 1 to 4 carbon atoms, a substituted or unsubstituted phenyl group, or a substituted or unsubstituted aralkyl group; h and i each independently represent an integer from 1 to 5; l and r each independently represent 0 or 1; V represents a group represented by any one of Formulae (VI-1) to (VI-11); and j and q each independently represent an integer from 0 to 2.

The polymerization degree p of the polymer according to the present invention represented by Formula (III-1) or (III-2) is preferably 5 to 5,000, and from the points of film-forming property, device stability, and the like, more preferably in the range of 10 to 1,000. The weight-average molecular weight Mw thereof is preferably in the range of 10,000 to 300,000.

As for the thiophene-containing compound and polymer according to the present invention, specific examples of the compounds having a structure represented by Formula (I) are listed in the following Tables 1 to 6, and specific examples of the compounds having a structure represented by Formula (III-1) or (III-2) are listed in the following Tables 7 to 9, but the compounds are not limited thereto. Among them, compounds having the fluorene, naphthalene, anthracene, or phenylene structure represented by the following formulae (11-1) to (II-5) as X are superior in mobility and quantum efficiency, practically useful, and thus, particularly preferable. The binding site in the Tables is a site inthte phenyl group numbered in Formula (I).

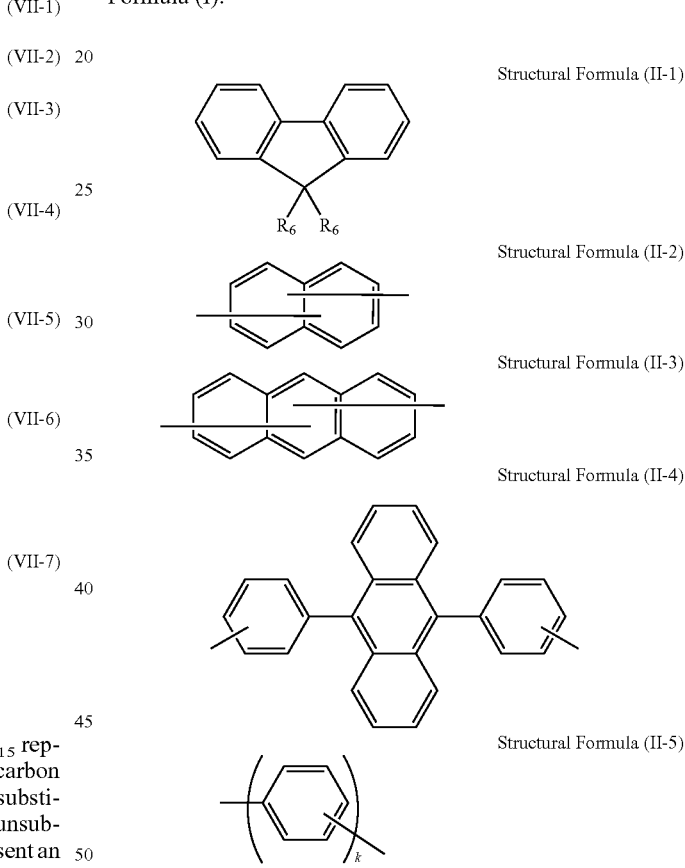

Structural Formula (II-1)
Structural Formula (II-2)
Structural Formula (II-3)
Structural Formula (II-4)
Structural Formula (II-5)

In Structural Formula (II-1), $R_6$ represents a hydrogen atom, an alkyl group, a substituted or unsubstituted aryl group, or a substituted or unsubstituted aralkyl group; and in Structural Formula (II-5), k represents an integer from 1 to 5.

TABLE 1

| Compound | k | l | m | $Ar_1$ | X | $R_1$ | $R_2$ | $R_3$ | $R_4$ | Binding Site |
|---|---|---|---|---|---|---|---|---|---|---|
| 1 | 1 | 1 | 0 | phenyl | — | H | H | H | H | 4 |

TABLE 1-continued
| Compound | k | l | m | Ar$_1$ | X | R$_1$ | R$_2$ | R$_3$ | R$_4$ | Binding Site |
|---|---|---|---|---|---|---|---|---|---|---|
| 2 | 1 | 1 | 1 | 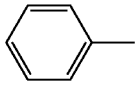 | 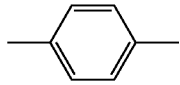 | H | H | H | H | 4 |
| 3 | 1 | 1 | 1 | 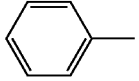 | 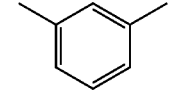 | H | H | H | H | 4 |
| 4 | 1 | 1 | 1 | 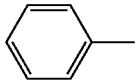 | 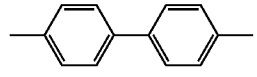 | H | H | H | H | 4 |
| 5 | 1 | 1 | 1 | 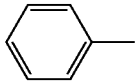 | 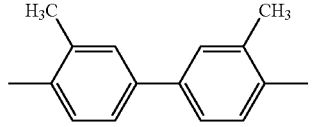 | H | H | H | H | 4 |
| 6 | 1 | 1 | 1 | 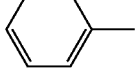 | 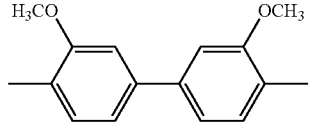 | H | H | H | H | 4 |
| 7 | 1 | 1 | 1 | 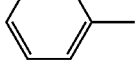 | 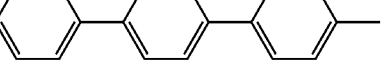 | H | H | H | H | 4 |
| 8 | 1 | 1 | 1 | 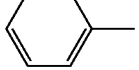 | 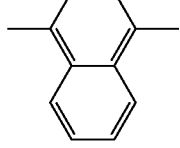 | H | H | H | H | 4 |
| 9 | 1 | 1 | 1 | 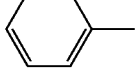 | 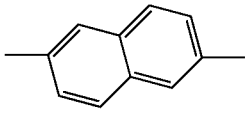 | H | H | H | H | 4 |
| 10 | 1 | 1 | 1 | 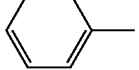 | 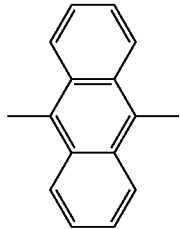 | H | H | H | H | 4 |
| 11 | 1 | 1 | 1 | 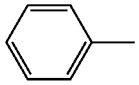 | 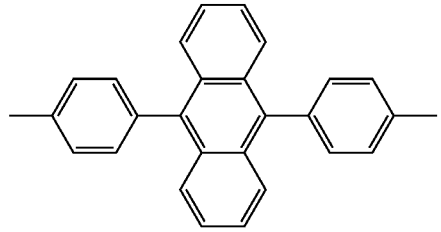 | H | H | H | H | 4 |

TABLE 1-continued
| Compound | k | l | m | Ar₁ | X | R₁ | R₂ | R₃ | R₄ | Binding Site |
|---|---|---|---|---|---|---|---|---|---|---|
| 12 | 1 | 1 | 1 | 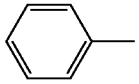 | 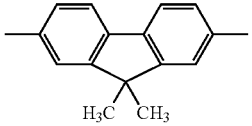 | H | H | H | H | 4 |
| 13 | 1 | 1 | 1 | 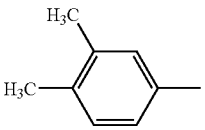 | 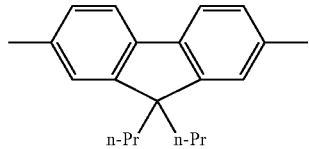 | H | H | H | H | 4 |
TABLE 2
| Compound | k | l | m | Ar₁ | X | R₁ | R₂ | R₃ | R₄ | Binding Site |
|---|---|---|---|---|---|---|---|---|---|---|
| 14 | 1 | 1 | 1 | 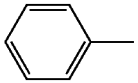 | 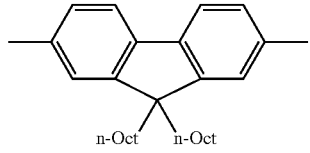 | H | H | H | H | 4 |
| 15 | 1 | 1 | 0 | 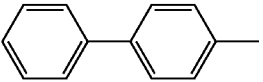 | — | H | H | H | H | 4 |
| 16 | 1 | 1 | 1 | 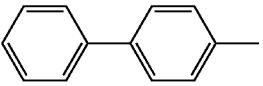 | 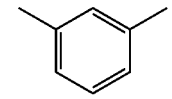 | H | H | H | H | 4 |
| 17 | 1 | 1 | 1 | 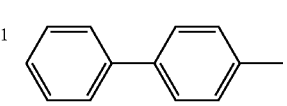 | 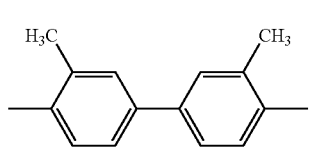 | H | H | H | H | 4 |
| 18 | 1 | 1 | 1 | 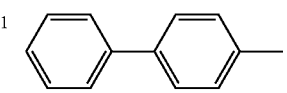 | 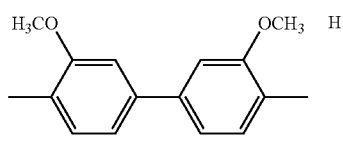 | H | H | H | H | 4 |
| 19 | 1 | 1 | 1 | 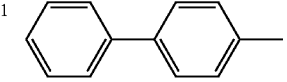 | 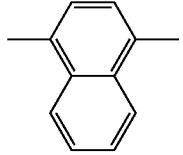 | H | H | H | H | 4 |
| 20 | 1 | 1 | 1 | 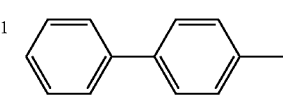 | 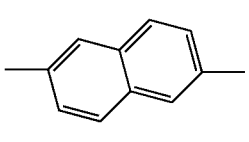 | H | H | H | H | 4 |

TABLE 2-continued
| Compound | k | l | m | Ar₁ | X | R₁ | R₂ | R₃ | R₄ | Binding Site |
|---|---|---|---|---|---|---|---|---|---|---|
| 21 | 1 | 1 | 1 | 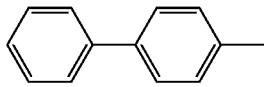 | 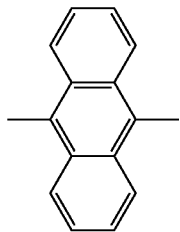 | H | H | H | H | 4 |
| 22 | 1 | 1 | 1 | 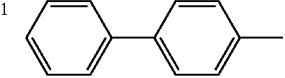 | 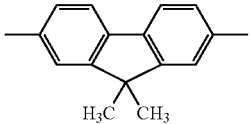 | H | H | H | H | 4 |
| 23 | 1 | 1 | 1 | 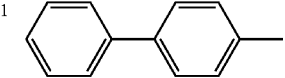 | 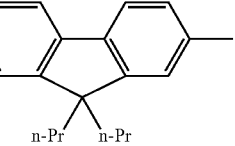 | H | H | H | H | 4 |
| 24 | 1 | 1 | 1 | 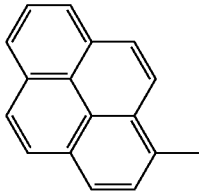 | 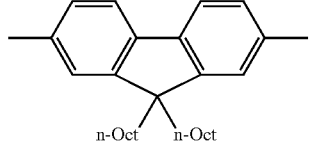 | H | H | H | H | 4 |
| 25 | 1 | 1 | 0 | 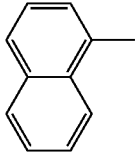 | — | H | H | H | H | 4 |
TABLE 3
| Compound | k | l | m | Ar₁ | X | R₁ | R₂ | R₃ | R₄ | Binding Site |
|---|---|---|---|---|---|---|---|---|---|---|
| 26 | 1 | 1 | 1 | 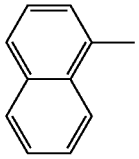 |  | H | H | H | H | 4 |
| 27 | 1 | 1 | 1 | 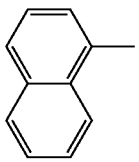 | 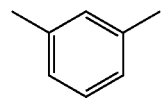 | H | H | H | H | 4 |

TABLE 3-continued
| Compound | k | l | m | Ar₁ | X | R₁ | R₂ | R₃ | R₄ | Binding Site |
|---|---|---|---|---|---|---|---|---|---|---|
| 28 | 1 | 1 | 1 | 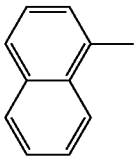 | 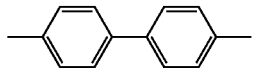 | H | H | H | H | 4 |
| 29 | 1 | 1 | 1 | 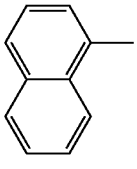 | 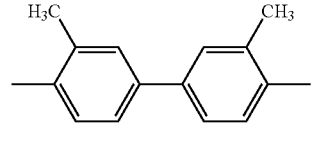 | H | H | H | H | 4 |
| 30 | 1 | 1 | 1 | 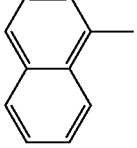 | 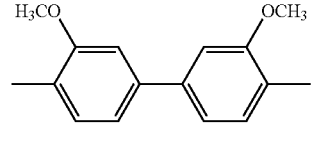 | H | H | H | H | 4 |
| 31 | 1 | 1 | 1 | 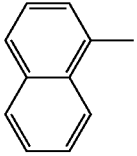 | 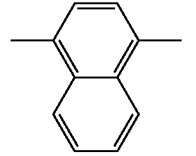 | H | H | H | H | 4 |
| 32 | 1 | 1 | 1 | 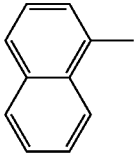 | 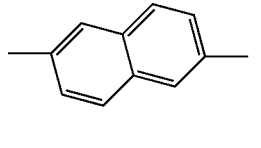 | H | H | H | H | 4 |
| 33 | 1 | 1 | 1 | 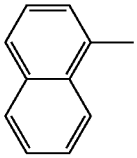 | 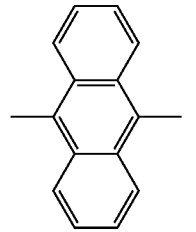 | H | H | H | H | 4 |
| 34 | 1 | 1 | 1 | 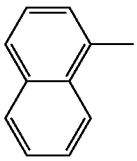 | 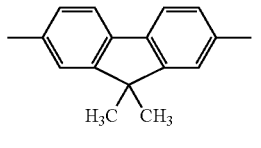 | H | H | H | H | 4 |
| 35 | 1 | 1 | 1 | 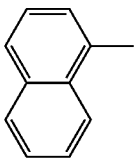 | 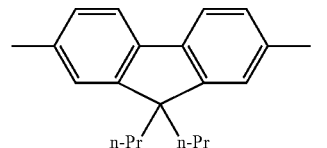 | H | H | H | H | 4 |

TABLE 3-continued

| Compound | k | l | m | Ar₁ | X | R₁ | R₂ | R₃ | R₄ | Binding Site |
|---|---|---|---|---|---|---|---|---|---|---|
| 36 | 1 | 1 | 1 | (phenanthrenyl) | (2,7-fluorenyl, 9,9-di-n-Oct) | H | H | H | H | 4 |

TABLE 4

| Compound | k | l | m | Ar₁ | X | R₁ | R₂ | R₃ | R₄ | Binding Site |
|---|---|---|---|---|---|---|---|---|---|---|
| 37 | 1 | 1 | 1 | (thiophene-phenyl) | C(CH₃)₃ (tert-butyl) | H | H | H | H | 4 |
| 38 | 1 | 1 | 1 | (thiophene-phenyl) | (1,3-phenylene) | H | H | H | H | 4 |
| 39 | 1 | 1 | 1 | (thiophene-phenyl) | (3,3'-dimethyl-4,4'-biphenylene) | H | H | H | H | 4 |
| 40 | 1 | 1 | 1 | (thiophene-phenyl) | (3,3'-dimethoxy-4,4'-biphenylene) | H | H | H | H | 4 |
| 41 | 1 | 1 | 1 | (thiophene-phenyl) | (1,4-naphthylene) | H | H | H | H | 4 |
| 42 | 1 | 1 | 1 | (thiophene-phenyl) | (9,10-anthrylene) | H | H | H | H | 4 |
| 43 | 1 | 1 | 1 | (thiophene-phenyl) | (2,7-fluorenyl, 9,9-di-n-Pr) | H | H | H | H | 4 |

TABLE 4-continued
| Compound | k | l | m | Ar₁ | X | R₁ | R₂ | R₃ | R₄ | Binding Site |
|---|---|---|---|---|---|---|---|---|---|---|
| 44 | 1 | 1 | 1 | 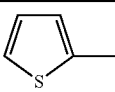 | 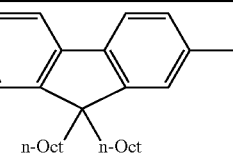 | H | H | H | H | 4 |
| 45 | 1 | 1 | 0 | 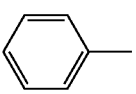 | — | H | H | H | H | 4 |
| 46 | 1 | 1 | 1 | 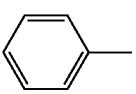 | 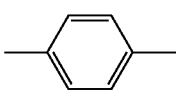 | CN | H | m-Xylyl- | H | 4 |
| 47 | 1 | 1 | 0 | 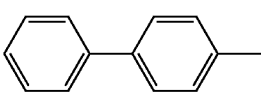 | — | CN | H | m-Xylyl- | H | 4 |
| 48 | 1 | 1 | 0 | 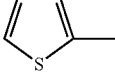 | — | CN | H | m-Xylyl- | H | 4 |
| 49 | 1 | 1 | 1 | 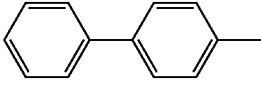 | 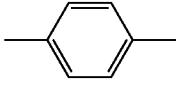 | CN | H | m-Xylyl- | H | 4 |
| 50 | 1 | 1 | 1 | 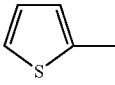 | 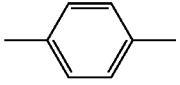 | CN | H | m-Xylyl- | H | 4 |
TABLE 5
| Compound | k | l | m | Ar₁ | X | R₁ | R₂ | R₃ | R₄ | Binding Site |
|---|---|---|---|---|---|---|---|---|---|---|
| 51 | 1 | 1 | 1 | 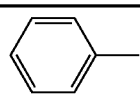 | 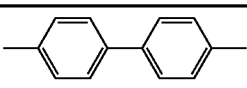 | CN | H | m-Xylyl- | H | 4 |
| 52 | 1 | 1 | 1 | 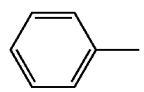 | 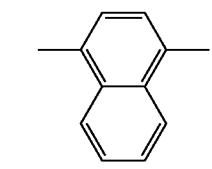 | CN | CN | m-Xylyl- | H | 4 |
| 53 | 1 | 1 | 1 | 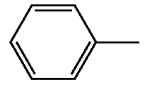 | 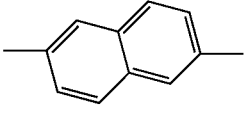 | CN | CN | m-Xylyl- | H | 4 |
| 54 | 1 | 1 | 1 | 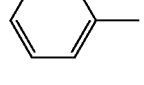 | 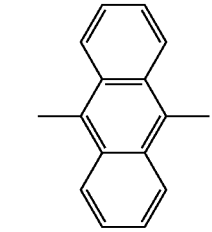 | CN | CN | m-Xylyl- | H | 4 |

TABLE 5-continued
| Compound | k | l | m | Ar₁ | X | R₁ | R₂ | R₃ | R₄ | Binding Site |
|---|---|---|---|---|---|---|---|---|---|---|
| 55 | 1 | 1 | 1 | 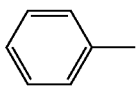 | 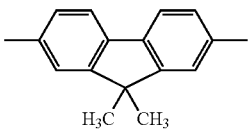 | CN | CN | m-Xylyl- | H | 4 |
| 56 | 0 | 1 | 0 | 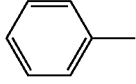 | — | H | H | H | H | 4 |
| 57 | 0 | 1 | 0 | 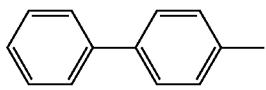 | — | H | H | H | H | 4 |
| 58 | 0 | 1 | 0 | 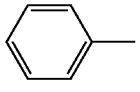 | — | H | H | H | m-Xylyl- | 4 |
| 58 | 0 | 2 | 0 | 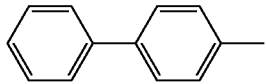 | — | H | H | H | m-Xylyl- | 4 |
| 59 | 0 | 2 | 0 | 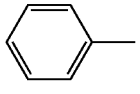 | — | H | H | n-Hex- | H | 4 |
| 60 | 0 | 2 | 0 | 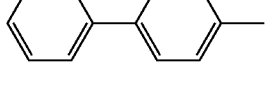 | — | H | H | n-Hex- | H | 4 |
| 61 | 0 | 2 | 0 | 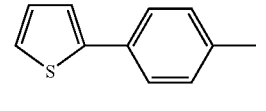 | — | H | H | m-Xylyl- | H | 4 |
| 62 | 1 | 1 | 0 | 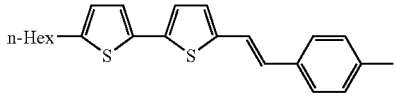 | — | H | H | H | m-Xylyl- | 4 |
| 63 | 1 | 1 | 0 | 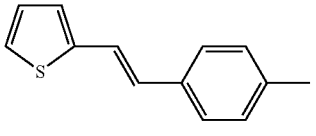 | — | H | H | H | m-Xylyl- | 4 |
TABLE 6
| Compound | k | l | m | Ar₁ | X | R₁ | R₂ | R₃ | R₄ | Binding Site |
|---|---|---|---|---|---|---|---|---|---|---|
| 64 | 1 | 1 | 0 | 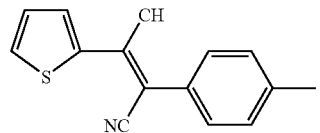 | — | CN | CN | H | m-Xylyl- | 4 |

TABLE 6-continued
| Compound | k | l | m | Ar₁ | X | R₁ | R₂ | R₃ | R₄ | Binding Site |
|---|---|---|---|---|---|---|---|---|---|---|
| 65 | 1 | 1 | 0 | 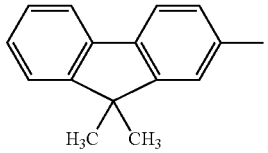 | — | CN | CN | m-Xylyl- | H | 4 |
TABLE 7
| Polymer | A Compound of Tables 1-6 | Ratio | Y | Z | m | p |
|---|---|---|---|---|---|---|
| (1) | 1 | — | —CH₂CH₂— | — | 1 | 98 |
| (2) | 1 | — | 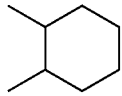 | — | 1 | 96 |
| (3) | 1 | — | 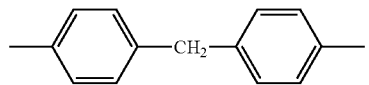 | — | 1 | 65 |
| (4) | 1 | — | 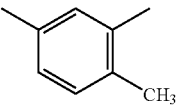 | — | 1 | 76 |
| (5) | 1 | — | 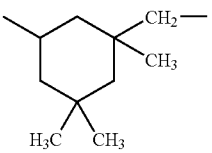 | — | 1 | 98 |
| (6) | 7 | — | —CH₂CH₂— | — | 1 | 73 |
| (7) | 9 | — | —CH₂CH₂— | — | 1 | 46 |
| (8) | 14 | — | —CH₂CH₂— | — | 1 | 82 |
| (9) | 14 | — | 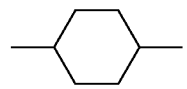 | — | 1 | 56 |
| (10) | 25 | — | —CH₂CH₂— | — | 1 | 102 |
| (11) | 25 | — | 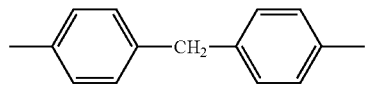 | — | 1 | 48 |
| (12) | 28 | — | —CH₂CH₂— | — | 1 | 92 |
| (13) | 28 | — | —(CH₂)₆— | — | 1 | 85 |
| (14) | 31 | — | —CH₂CH₂— | — | 1 | 135 |
| (15) | 36 | — | —CH₂CH₂— | — | 1 | 45 |
| (16) | 36 | — | 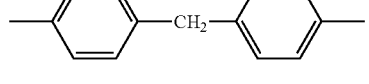 | — | 1 | 68 |

TABLE 7-continued

| Polymer | A Compound of Tables 1-6 | Ratio | Y | Z | m | p |
|---|---|---|---|---|---|---|
| (17) | 39 | — | —CH₂CH₂— | — | 1 | 96 |
| (18) | 41 | — | —CH₂CH₂— | — | 1 | 79 |
| (19) | 41 | — | —(CH₂)₆— | — | 1 | 100 |
| (20) | 41 | — | —C₆H₄—CH₂—C₆H₄— | — | 1 | 112 |
| (21) | 42 | — | —CH₂CH₂— | — | 1 | 72 |
| (22) | 42 | — | —C₆H₄—CH₂—C₆H₄— | — | 1 | 102 |
| (23) | 42 | — | 2,4-dimethylphenyl (with CH₃) | — | 1 | 100 |
| (24) | 45 | — | —CH₂CH₂— | — | 1 | 67 |
| (25) | 45 | — | —(CH₂)₆— | — | 1 | 87 |

TABLE 8

| Polymer | A Compound of Tables 1-6 | Ratio | Y | Z | m | p |
|---|---|---|---|---|---|---|
| (26) | 45 | — | —C₆H₄—CH₂—C₆H₄— | — | 1 | 86 |
| (27) | 45 | — | —H₂C—C₆H₄—CH₂— (meta) | — | 1 | 96 |
| (28) | 52 | — | —CH₂CH₂— | — | 1 | 75 |
| (29) | 53 | — | —CH₂CH₂— | — | 1 | 96 |
| (30) | 53 | — | —C₆H₄—CH₂—C₆H₄— | — | 1 | 93 |
| (31) | 58 | — | —CH₂CH₂— | — | 1 | 89 |
| (32) | 61 | — | —CH₂CH₂— | — | 1 | 56 |
| (33) | 61 | — | —C₆H₄—CH₂—C₆H₄— | — | 1 | 42 |
| (34) | 1/9 | 1/1 | —CH₂CH₂— | — | 1 | 77 |

TABLE 8-continued

| Polymer | A Compound of Tables 1-6 | Ratio | Y | Z | m | p |
|---|---|---|---|---|---|---|
| (35) | 1/9 | 1/1 | -C₆H₄-CH₂-C₆H₄- | — | 1 | 110 |
| (36) | 1/42 | 1/1 | —CH₂CH₂— | — | 1 | 106 |
| (37) | 14/42 | 1/1 | —CH₂CH₂— | — | 1 | 100 |
| (38) | 14/45 | 1/1 | —CH₂CH₂— | — | 1 | 66 |
| (39) | 14/63 | 1/1 | —CH₂CH₂— | — | 1 | 49 |
| (40) | 42/45 | 1/1 | —CH₂CH₂— | — | 1 | 89 |
| (41) | 1/15 | 1/1 | -C₆H₄-CH₂-C₆H₄- | — | 1 | 56 |
| (42) | 1/42 | 1/1 | -C₆H₄-CH₂-C₆H₄- | — | 1 | 98 |
| (43) | 14/42 | 1/1 | -C₆H₄-CH₂-C₆H₄- | — | 1 | 75 |
| (44) | 14/45 | 1/1 | -C₆H₄-CH₂-C₆H₄- | — | 1 | 100 |
| (45) | 42/45 | 1/1 | -C₆H₄-CH₂-C₆H₄- | — | 1 | 56 |
| (46) | 16/22 | 1/1 | —CH₂CH₂— | — | 1 | 88 |
| (47) | 101 | — | —CH₂CH₂— | — | 1 | 65 |
| (48) | 104 | — | —CH₂CH₂— | — | 1 | 89 |
| (49) | 108 | — | —CH₂CH₂— | — | 1 | 75 |
| (50) | 109 | — | —CH₂CH₂— | — | 1 | 74 |

TABLE 9

| Polymer | A Compound of Tables 1-6 | Ratio | Y | Z | m | p |
|---|---|---|---|---|---|---|
| (51) | 110 | — | —CH₂CH₂— | — | 1 | 54 |
| (52) | 119 | — | —CH₂CH₂— | — | 1 | 66 |
| (53) | 121 | — | —CH₂CH₂— | — | 1 | 68 |
| (54) | 125 | — | —CH₂CH₂— | — | 1 | 105 |
| (55) | 131 | — | —CH₂CH₂— | — | 1 | 84 |
| (56) | 135 | — | —CH₂CH₂— | — | 1 | 88 |
| (57) | 138 | — | —CH₂CH₂— | — | 1 | 111 |
| (58) | 145 | — | —CH₂CH₂— | — | 1 | 102 |

TABLE 9-continued

| Polymer | A Compound of Tables 1-6 | Ratio | Y | Z | m | p |
|---|---|---|---|---|---|---|
| (59) | 152 | — | —CH$_2$CH$_2$— | — | 1 | 98 |
| (60) | 155 | — | —CH$_2$CH$_2$— | — | 1 | 67 |
| (61) | 104 | — | —C$_6$H$_4$—CH$_2$—C$_6$H$_4$— | — | 1 | 66 |
| (62) | 123 | — | —C$_6$H$_4$—CH$_2$—C$_6$H$_4$— | — | 1 | 109 |
| (63) | 109/121 | 1/1 | —CH$_2$CH$_2$— | — | 1 | 89 |
| (64) | 109/145 | 1/1 | —CH$_2$CH$_2$— | — | 1 | 84 |
| (65) | 109/152 | 1/1 | —CH$_2$CH$_2$— | — | 1 | 76 |
| (66) | 109/121 | 1/1 | —C$_6$H$_4$—CH$_2$—C$_6$H$_4$— | — | 1 | 78 |
| (67) | 109/145 | 1/1 | —C$_6$H$_4$—CH$_2$—C$_6$H$_4$— | — | 1 | 56 |
| (68) | 1 | — | — | —CH$_2$CH$_2$— | 1 | 65 |
| (69) | 7 | — | — | —CH$_2$CH$_2$— | 1 | 95 |
| (70) | 9 | — | — | —CH$_2$CH$_2$— | 1 | 93 |
| (71) | 14 | — | — | —CH$_2$CH$_2$— | 1 | 78 |
| (72) | 25 | — | — | —CH$_2$CH$_2$— | 1 | 85 |
| (73) | 41 | — | — | —CH$_2$CH$_2$— | 1 | 63 |
| (74) | 42 | — | — | —CH$_2$CH$_2$— | 1 | 46 |
| (75) | 45 | — | — | —CH$_2$CH$_2$— | 1 | 74 |
| (76) | 53 | — | — | —CH$_2$CH$_2$— | 1 | 73 |

The thiophene-containing compound according to the invention can be synthesized, for example, by the following method (1) or (2), depending on its structure.

(1) Synthesis of a diarylamine from an arylamine and a halogenated carboalkoxyalkylbenzene, or from an aryl halide and a carboalkoxyaniline, and subsequent reaction thereof with an aryl dihalide.

(2) Synthesis of a diarylamine in the same manner as in (1) above, reaction thereof with an aryl halide to give a triarylamine derivative, and subsequent halogenation and homo-coupling of the triarylamine derivative thus obtained.

About a synthesis of a charge-transporting material having an alkylenecarboxylic acid ester, JP-A No. 5-80550, the disclosure of which is incorporated by reference herein, describes a process of introducing a chloromethyl group to a skeleton, producing a Grignard reagent with Mg, converting the reagent into a carboxylic acid with carbon dioxide, and esterifying the acid. In this process, however, the reactivity of the chloromethyl group is high, therefore, the chloromethyl group cannot be introduced in raw material at the initial stage of synthesis.

It is therefore necessary to form a skeleton of a triarylamine, a tetraarylbenzidine or the like, and convert the methyl group introduced to the raw material at the initial stage of synthesis to a chloromethyl, or use an unsubstituted raw material, form a tetraarylbenzidine skeleton, and introduce a functional group such as a formyl group thereto by a substitution reaction to the aromatic ring, reduce the resultant to prepare an alcohol, and convert the alcohol to a chloromethyl group with a halogenating reagent such as thionyl chloride, or perform direct chloromethylation with paraformaldehyde and hydrochloric acid.

However, the charge-transporting material having a skeleton of a triarylamine, a tetraarylbenzidine or the like has a very high reactivity, therefore, according to the process of chloromethylation of the introduced methyl group, a substitution reaction of halogen to the aromatic ring is easily caused. As a result, it is substantially impossible to chlorinate only the methyl group selectively.

According to the process of using an unsubstituted raw material at the initial stage, introducing a functional group such as a formyl group thereto, and converting the functional group to a chloromethyl group, or the direct chloromethylation process, the chloromethyl group can be introduced to only the para-position with respect to the nitrogen atom. Accordingly, an alkylenecarboxylic acid ester group can be introduced to only the para-position with respect to the nitrogen atom. In the process of the introduction of a formyl group and subsequent conversion of the group to a chloromethyl group, the steps of the reactions are too long. On the other hand, the process of reacting an arylamine, diarylbenzidine or the like with a halogenated carboalkoxyalkylbenzene to yield a monomer is superior because it is easy to change the position of a substituent to control ionization potential or the like. Thus, it becomes possible to control the compound. Since the monomer used in the synthesis of the polymer of the invention can have one or more selected from various substituents at arbitrary position(s) and is chemically stable, the monomer can easily be handled. Thus, the above-mentioned problems can be solved.

The method of producing the thiophene-containing compound according to the invention will be described concretely. In the invention, a diarylamine represented by the following Formula (XIII) is obtained first in "coupling reaction of a compound represented by the following Formula (IX) and a compound represented by the following Formula (X) by a copper catalyst", or "coupling reaction of a compound represented by the following Formula (XI) and a compound represented by the following Formula (XII) by a copper catalyst". Subsequent coupling reaction of the diarylamine (represented by the following Formula XIII) with a compound represented by the following Formula (XIV) by a copper catalyst gives a thiophene-containing compound according to the present invention.

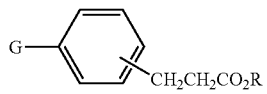

(IX)

In Formula (IX), R represents a hydrogen atom, an alkyl group, a substituted or unsubstituted aryl group, or a substituted or unsubstituted aralkyl group; and G represents a bromine atom or an iodine atom.

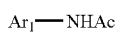

(X)

In Formula (X), $Ar_1$ is the same as that described above (in Formula (I)).

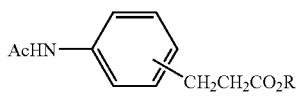

(XI)

In Formula (XI), R represents a hydrogen atom, an alkyl group, a substituted or unsubstituted aryl group, or a substituted or unsubstituted aralkyl group.

(XII)

In Formula (XII), $Ar_1$ and G are the same as those described above (in Formulae (IX) and (X)).

(XIII)

In Formula (XIII), $Ar_1$ is the same as that described in Formula (I), and R is the same as that described in Formula (XI).

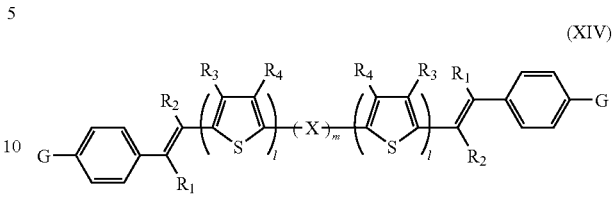

(XIV)

In Formula (XIV), X, $R_1$ to $R_4$, l and m are the same as those described in Formula (I); and G is the same as that described in Formula (IX).

In the coupling reaction, the halogen compound represented by Formula (IX) or (XII) can be used in an amount of 0.5 to 1.5 equivalents, and preferably 0.7 to 1.2 equivalents per 1 equivalent of the acetyl compound represented by Formula (X) or (XI). The copper catalyst used may be copper powder, cuprous oxide, copper sulfate, or the like; and the copper catalyst can be used in an amount of 0.001 to 3 parts by weight, and preferably 0.01 to 2 parts by weight per 1 part by weight of the acetyl compound represented by Formula (X) or (XI).

The base for use in the coupling reaction may be sodium hydroxide, potassium hydroxide, sodium carbonate, potassium carbonate, or the like, and the base can be used in an amount of 0.5 to 3 equivalents, and preferably 0.7 to 2 equivalents per 1 equivalent of the acetyl compound represented by Formula (X) or (XI).

The coupling reaction does not necessarily demand a solvent, but, if used, favorable solvents include high-boiling point non-aqueous hydrocarbon solvents such as n-tridecane, tetralin, p-cymene and terpinolene, high-boiling point halogenated solvents such as o-dichlorobenzene and chlorobenzene, and the like; and the solvent can be used in an amount in the range of 0.1 to 3 parts by weight, and preferably 0.2 to 2 parts by weight per 1 part by weight of the acetyl compound represented by Formula (X) or (XI).

The reaction is preferably carried out at a temperature in the range of 100 to 300° C., preferably 150 to 270° C., and more preferably 180 to 230° C., under the atmosphere of an inert gas such as nitrogen or argon, while the mixture is stirred sufficiently and efficiently and water generated during reaction is removed. After the termination of the reaction, the product is cooled as needed, and then is preferably hydrolyzed by using a base such as sodium hydroxide or potassium hydroxide and a solvent such as methanol, ethanol, n-octanol, ethylene glycol, propylene glycol, or glycerol.

In such a case, the amount of the solvent used may be 0.5 to 10 parts by weight, and preferably 1 to 5 parts by weight per 1 part by weight of the acetyl compound represented by Formula (X) or (XI), and the amount of the base may be 0.2 to 5 parts by weight, and preferably 0.3 to 3 parts by weight per 1 part by weight of the acetyl compound represented by Formula (X) or (XI).

After the coupling reaction, the hydrolysis reaction is carried out by adding a solvent and a base directly to the reaction solution and stirring the mixture sufficiently and efficiently at a temperature in the range from 50° C. to the boiling point of the solvent under the atmosphere of an inert gas such as nitrogen or argon. In such a case, the solvent used is preferably a high-boiling point solvent having a boiling point of 150° C. or higher that allows increase in reaction temperature for prevention of solidification of the carboxylate salt generated in the coupling reaction; and addition of an aqueous solvent such as ethylene glycol, propylene glycol, or glycerol is particularly preferable, for liberating the compound represented by Formula (XIII) after addition of water and neutralization, for example, with hydrochloric acid in posttreatment.

After the termination of the hydrolysis reaction, the reaction product is poured into water and neutralized, for example, with hydrochloric acid, to give a free compound represented by Formula (XIII), which is then, washed thoroughly, dissolved in a suitable solvent as needed, purified by chromatography in a column of silica gel, alumina, activated clay, activated carbon or the like or adsorption of undesired components with the adsorbent added to the solution, and further purified by recrystallization in a suitable solvent such as acetone, ethanol, ethyl acetate, or toluene; or alternatively, the free compound may be first esterified, for example, to a methyl or ethyl ester and then processed in a similar manner.

Then, the compound represented by Formula (XIII) thus obtained is allowed to react with a compound represented by Formula (XIV) in coupling reaction by a copper catalyst and esterified, for example, to a methyl or ethyl ester, or the compound represented by Formula (XIII) is first esterified, for example, to a methyl or ethyl ester and then allowed to react with a compound represented by Formula (XIV) in coupling reaction by a copper catalyst, to give an amine compound represented by Formula (I).

When a dihalogenated compound is used as the compound represented by Formula (XIV) in the coupling reaction between the compound represented by Formula (XIII) and the compound represented by Formula (XIV), the compound represented by Formula (XIV) can be used in an amount of 1.5 to 5 equivalents, and preferably 1.7 to 4 equivalents per 1 equivalent of the compound represented by Formula (XIII).

The copper catalyst used may be copper powder, cuprous oxide, copper sulfate, or the like, and the copper catalyst can be used in an amount of 0.001 to 3 parts by weight, and preferably 0.01 to 2 parts by weight per 1 part by weight of the compound represented by Formula (XIII). The base used may be sodium hydroxide, potassium hydroxide, sodium carbonate, potassium carbonate, or the like, and the base can be used in an amount of 1 to 6 equivalents, and preferably 1.4 to 4 equivalents per 1 equivalent of the compound represented by Formula (XIII).

A solvent is used as needed, and favorable solvents if used include high-boiling point non-aqueous hydrocarbon solvents such as n-tridecane, tetralin, p-cymene, and terpinolene, high-boiling point halogenated solvents such as o-dichlorobenzene and chlorobenzene, and the like; and the solvent can be used in an amount of 0.1 to 3 parts by weight, and preferably 0.2 to 2 parts by weight per 1 part by weight of the compound represented by Formula (XIII).

The reaction is preferably carried out at 100 to 300° C., preferably 150 to 270° C. and more preferably 180 to 250° C., under the atmosphere of an inert gas such as nitrogen or argon, while the mixture is stirred sufficiently and efficiently and water generated during the reaction is removed.

After the termination of the reaction, the reaction product is dissolved in a solvent such as toluene, ISOPAR, or n-tridecane, washed with water or filtered as needed for removal of undesirable substances, purified, for example, by chromatography in a column of silica gel, alumina, activated clay, activated carbon, or the like, or adsorption of undesirable components by addition of the adsorbent to the solution, and further purified by recrystallization in a suitable solvent such as ethanol, ethyl acetate, or toluene.

When a monohalogenated compound is used as the compound represented by Formula (XIV) in the coupling reaction, a copper catalyst and a base, as well as a solvent as needed, are used together with the compound represented by Formula (XIV).

The copper catalyst may be copper powder, cuprous oxide, copper sulfate, or the like, and the copper catalyst can be used in an amount of 0.001 to 3 parts by weight, and preferably, 0.01 to 2 parts by weight per part by weight of the compound represented by Formula (XIII).

The base for use may be sodium hydroxide, potassium hydroxide, sodium carbonate, potassium carbonate, or the like, and the base can be used in an amount of 0.5 to 3 equivalents, and preferably 0.7 to 2 equivalents per 1 equivalent of the compound represented by Formula (XIII).

The solvents favorably used include high-boiling point non-aqueous hydrocarbon solvents such as n-tridecane, tetralin, p-cymene, and terpinolene and high-boiling point halogenated solvents such as o-dichlorobenzene and chlorobenzene; and the solvent can be used in an amount of 0.1 to 3 parts by weight, and preferably 0.2 to 2 parts by weight per 1 part by weight of the compound represented by Formula (XIII). The reaction, post-treatment, and purification thereof are carried out in the same manner as the case where a dihalogenated compound is used as the compound represented by Formula (XIV).

When a dihalogenated compound is used, X in Formula (I) is preferably one of the following groups (represented by the following Structural Formulae (II-1) to (II-5)), for improvement in mobility and quantum efficiency.

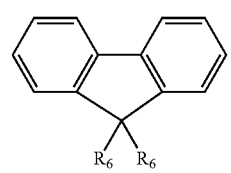

Structural Formula (II-1)

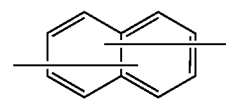

Structural Formula (II-2)

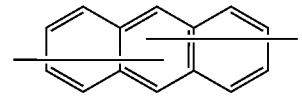

Structural Formula (II-3)

Structural Formula (II-4)

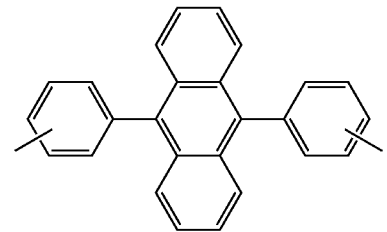

Structural Formula (II-5)

In Structural Formula (II-1), $R_6$ represents a hydrogen atom, an alkyl group, a substituted or unsubstituted aryl group, or a substituted or unsubstituted aralkyl group; and, in Structural Formula (II-5), k represents an integer from 1 to 5.]

The thiophene-containing compound according to the invention can also be synthesized by preparing a triarylamine represented by the following Formula (XV) in the coupling reaction by a copper catalyst in a similar manner to above and then converting the triarylamin into a compound represented the following Formula (XVI) by halogenation, for example, with N-bromosuccinic acid imide (NBS) or N-chlorosuccinic acid imide (NCS), and subjecting the compound represented by Formula (XVI) to the homocoupling reaction by using a nickel catalyst.

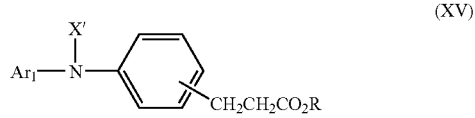

(XV)

In Formula (XV), $Ar_1$ is the same as that described above; X' represents a substituted or unsubstituted divalent aromatic group or a substituted or unsubstituted divalent aromatic group containing one or more thiophene rings; and R represents a hydrogen atom, an alkyl group, a substituted or unsubstituted aryl group, or a substituted or unsubstituted aralkyl group.

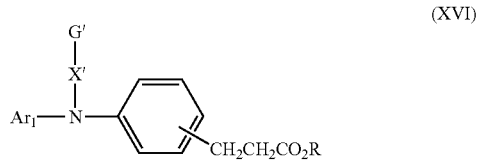

(XVI)

In Formula (XVI), $Ar_1$, X' and R are the same as those described above, and G' represents a bromine or chlorine atom.

The homocoupling reaction is preferably performed in the combination of a compound represented by Formula (XVI), a nickel complex, triphenylphosphine, and zinc in a solvent. If the halogen atom to be introduced is chlorine, it is possible to introduce the halogen atom by halogenation before forming a triarylamine skeleton in the coupling reaction by a copper catalyst.

Examples of the nickel complexes used in the reaction include nickel chloride, nickel bromide, nickel acetate, and the like; and the complex can be used in an amount of 0.001 to 3 equivalents, preferably, 0.1 to 2 equivalents, with respect to 1 equivalent of the compound represented by Formula (XVI).

The reaction is preferably carried out in the presence of a reducing agent such as zinc; and the reducing agent can be used in an amount of 0.001 to 3 equivalents, and preferably 0.1 to 2 equivalents per 1 equivalent of the compound represented by Formula (XVI). In addition, triphenylphosphine can be used in an amount of 0.5 to 3 equivalents, and preferably 0.7 to 2 equivalents per 1 equivalent of the compound represented by Formula (XVI). Examples of the solvents for use in the reaction include dimethylformamide (DMF), dimethylacetamide (DMA), tetrahydrofuran (THF), dimethoxyethane (DME), N-methylpyrrolidone (No), and the like, and the solvent can be used in an amount of 0.1 to 10 equivalents, and preferably 2 to 5 equivalents per 1 equivalent of the compound represented by Formula (XVI).

In addition, the reaction is preferably carried out at a temperature in the range of 0 to 100° C., preferably of room temperature to 50° C., under the atmosphere of an inert gas such as nitrogen or argon, while the mixture is stirred sufficiently and efficiently. After the termination of the reaction, the reaction solution is poured into water and stirred well therein; and if the reaction product is crystalline, a crude product can be obtained by suction filtration. If the reaction product is oily, a crude product can be obtained by extraction with a suitable solvent such as ethyl acetate or toluene.

The crude product thus obtained is purified by chromatography in a column of silica gel, alumina, activated clay, activated carbon, or the like or adsorption of undesirable components by addition of the absorbent to the solution, and additionally by recrystallization in a suitable solvent such as hexane, methanol, acetone, ethanol, ethyl acetate, or toluene, if the reaction product is crystalline.

The polymers represented by Formula (III-1) or (III-2) according to the invention can be synthesized by polymerizing a monomer represented by the following formula (XVII) according to a known method, for example, that described in New Experimental Chemistry Vol. 28, 4th Ed., (Chemical Society of Japan Ed., Maruzen), the disclosure of which is incorporated by reference herein.

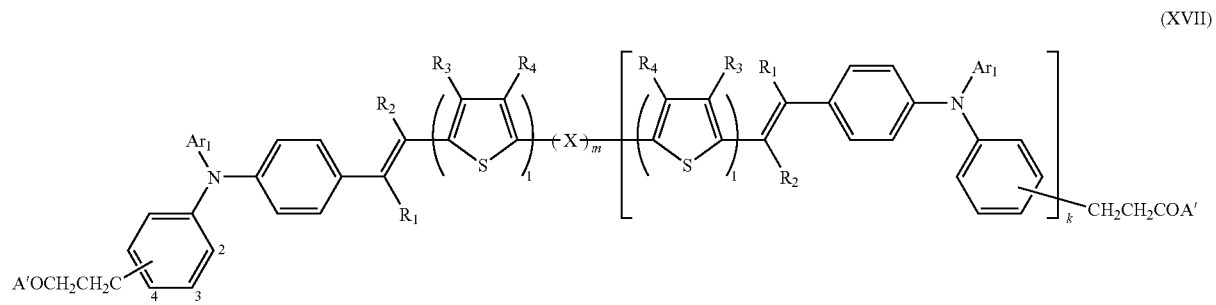

(XVII)

In Formula (XVII), $Ar_1$, X, and others are the same as those described in Formula (I); and A' represents a hydroxyll group, a halogen atom, or a group —O—R (R represents an alkyl group, a substituted or unsubstituted aryl group or an aralkyl group).

The thiophene-containing compound polymers represented by Formulae (III-1) or (III-2) can be synthesized in the following manner:

(1) In the case in which A' is a hydroxyl group:

In the case in which A' in Formula (XVII) is a hydroxyl group, a divalent alcohol represented by HO—$(Y-O)_m$—H (m represents an integer from 1 to 5, and the same is true in case of (2) and (3) below) is mixed with the monomer in substantially equivalent amounts, and they are polymerized with an acid catalyst. As the acid catalyst, a catalyst which is used for ordinary esterifying reaction can be used. Examples thereof include sulfuric acid, toluene sulfonic acid, and trifluoroacetic acid. The catalyst can be used in an amount of 1/1,0000 to 1/10 part by weight, and preferably 1/1,000 to 1/50 part by weight per 1 part by weight of the monomer.

In order to remove water produced in the synthesis, it is preferable to use a solvent azeotropic with water. Effective examples thereof include toluene, chlorobenzene and 1-chloronaphthalene. The solvent is used in an amount of 1 to 100 parts by weight, and preferably 2 to 50 parts by weight per 1 part by weight of the monomer.

Reaction temperature can be arbitrarily set. In order to remove water produced in the polymerization, it is preferable to conduct the reaction at the boiling point of the solvent. In the case in which no solvent has been used, the resultant product is dissolved in a suitable solvent in which the product can be dissolved after the end of the reaction. In the case in which the solvent is used, the reaction solution is dropped, as it is, into a poor solvent, in which a polymer is not easily dissolved, for example, acetone, or an alcohol such as methanol or ethanol, so as to precipitate the polymer. The polymer is isolated and subsequently the polymer is sufficiently washed with water or an organic solvent and dried. If necessary, a reprecipitation treatment, which comprises the steps of dissolving the polymer in a suitable organic solvent and dropping the solution into a poor solvent to precipitate the polymer, may be repeated.

In the reprecipitation treatment, it is preferable to perform stirring effectively with a mechanical stirrer or the like. The solvent for dissolving the polymer in the reprecipitation treatment can be used in an amount of 1 to 100 parts by weight, and preferably 2 to 50 parts by weight per 1 part by weight of the polymer. The poor solvent can be used in an amount of 1 to 1,000 parts by weight, and preferably 10 to 500 parts by weight per 1 part by weight of the polymer.

(2) In the case in which A' is a halogen:

In the case in which A' in Formula (XVII) is a halogen, a divalent alcohol represented by HO—$(Y-O)_m$—H is mixed with the monomer in substantially equivalent amounts, and they are polymerized with an organic basic catalyst such as pyridine or triethylamine. The organic basic catalyst can be used in an amount of 1 to 10 equivalents, and preferably 2 to 5 equivalents per 1 part by weight of the monomer.

As a solvent, methylene chloride, tetrahydrofuran (THF), toluene, chlorobenzene, 1-chloronaphthalene or the like is effective. The solvent can be used in an amount of 1 to 100 parts by weight, and preferably 2 to 50 parts by weight per 1 part by weight of the monomer.

Reaction temperature can be arbitrarily set. After the polymerization, reprecipitation treatment is conducted as described above, so as to perform purification. In the case in a divalent alcohol having a high acidity, such as bisphenol, interfacial polymerization may be used. That is, water is added to the divalent alcohol and an equivalent amount of a base is added thereto, so as to dissolve the base. Thereafter, the solution is vigorously stirred and simultaneously a monomer is added to the solution. The amount of the monomer is an amount equivalent to the divalent alcohol. At this time, water can be used in an amount of 1 to 1,000 parts by weight, and preferably 2 to 500 parts by weight per 1 part by weight of the divalent alcohol. Effective examples of the solvent for dissolving monomer include methylene chloride, dichloroethane, trichloroethane, toluene, chlorobenzene, and 1-chloronaphthalene.

Reaction temperature can be arbitrarily set. In order to promote the reaction, it is effective to use a phase transfer catalyst such as an ammonium salt or a sulfonium salt. The phase transfer catalyst can be used in an amount of 0.1 to 10 parts by weight, and preferably 0.2 to 5 parts by weight per 1 part by weight of the monomer.

(3) In the case in which A' is —O—R:

In the case in which A' in Formula (XVII) is —O—R, an excessive amount of a divalent alcohol represented by HO—$(Y-O)_m$—H is added to the monomer, and then the solution is heated with, as a catalyst, an inorganic acid such as sulfuric acid or phosphoric acid, a titanium alkoxide, an acetate or carbonate of calcium, cobalt or the like, or zinc oxide, so as to perform ester interchange. In this way, a polymer can be synthesized.

The divalent alcohol can be used in an amount of 2 to 100 equivalents, and preferably 3 to 50 equivalents per 1 equivalent of the monomer. The catalyst can be used in an amount of 1/1,000 to 1 part by weight, and preferably 1/100 to 1/2 part by weight per 1 part by weight of the monomer.

The reaction is conducted at a reaction temperature of 200 to 300° C. After the end of the ester interchange from the group —O—$R_{12}$ to the group —O—$(Y-O-)_n$—H, in order to promote polymerization reaction by elimination of the group HO—$(Y-O-)_m$—H, the reaction is preferably conducted under reduced pressure. A high boiling point solvent which can be azeotropic with the group HO—$(Y-O-)_m$—H, such as 1-chloronaphthalene, can be used to remove the group HO—$(Y-O-)_m$—H under reduced pressure and simultaneously the reaction can be advanced.

Alternatively, the thiophene-containing compound polymers represented by Formula (III-1) or (III-2) can be synthesized in the following manner. In each case above, a polymer can be prepared by first preparing a compound represented by the following formula (XVIII) in a reaction in the presence of an excess amount of divalent alcohol, and allowing it to react as a monomer, for example, with a divalent carboxylic acid or a divalent carboxylic acid halide in a similar manner to (2) above.

(XVIII)

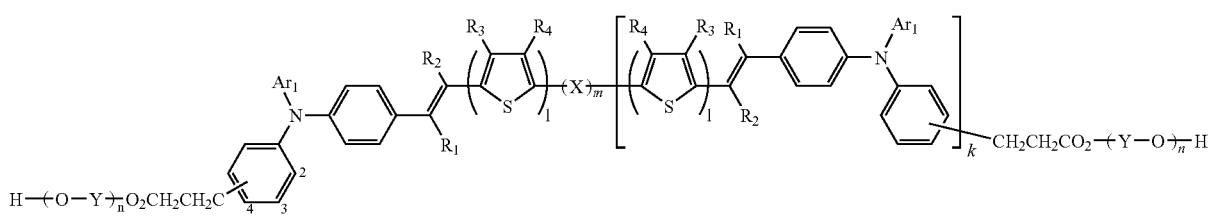

In Formula (XVIII), $Ar_1$, X, $R_1$ to $R_5$, 1, m, and k are the same as $Ar_1$, X, $R_1$ to $R_5$, 1, m, and k described in Formula (I) above; Y represents a divalent hydrocarbon group; and n represents an integer from 1 to 5.

Hereinafter, embodiments of the invention will be described. However, the invention is not limited to these embodiments.

According to an aspect of the invention, a thiophene-containing compound represented by Formula (I) is provided.

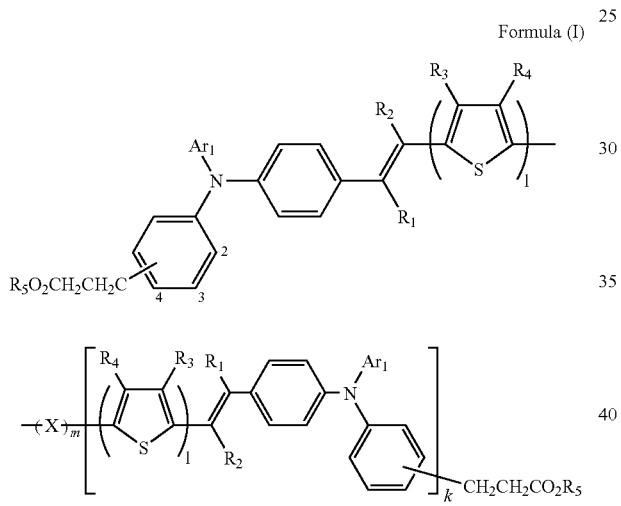

Formula (I)

In Formula (I), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_5$ each independently represent a hydrogen atom, an alkyl group, a cyano group, a halogen group, a substituted amino group, a substituted or unsubstituted aryl group, or a substituted or unsubstituted aralkyl group; 1 represents an integer from 1 to 5; and m and k each independently represent 0 or 1.

In Formula (I), X may represent a divalent straight-chain hydrocarbon group having 2 to 6 carbon atoms, a divalent branched-chain hydrocarbon group having 3 to 7 carbon atoms, a substituted or unsubstituted divalent polynuclear aromatic hydrocarbon having 1 to 8 aromatic rings, a substituted or unsubstituted divalent condensed aromatic hydrocarbon having 1 to 8 aromatic rings, or a substituted or unsubstituted divalent aromatic heterocyclic ring having 1 to 11 heterocyclic rings.

In Formula (I), X may represent a group represented by one selected from the group consisting of Structural Formulae (II-1) to (II-5).

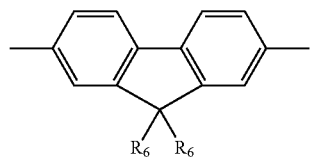

Structural Formula (II-1)

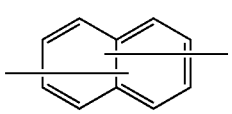

Structural Formula (II-2)

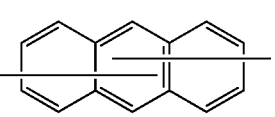

Structural Formula (II-3)

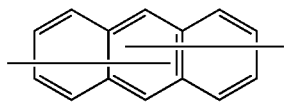

Structural Formula (II-4)

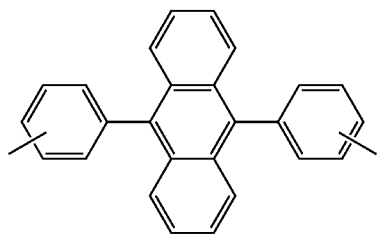

Structural Formula (II-5)

In Structural Formula (II-1), $R_6$ represents a hydrogen atom, an alkyl group, a substituted or unsubstituted aryl group, or a substituted or unsubstituted aralkyl group; and in Structural Formula (II-5), k represents an integer from 1 to 5.

In Formula (I), $Ar_1$ may represent a substituted or unsubstituted phenyl group.

In Formula (I), $Ar_1$ may represent a substituted or unsubstituted monovalent polynuclear aromatic hydrocarbon having 2 to 20 aromatic rings.

In Formula (I), $Ar_1$ may represent a substituted or unsubstituted monovalent condensed aromatic hydrocarbon having 2 to 20 aromatic rings.

In Formula (I), $Ar_1$ may represent a substituted or unsubstituted monovalent aromatic heterocyclic ring.

In Formula (I), $Ar_1$ may represent a substituted or unsubstituted monovalent aromatic group containing at least one aromatic heterocyclic ring.

According to another aspect of the invention, a thiophene-containing compound polymer represented by Formula (III-1) or (III-2) is provided.

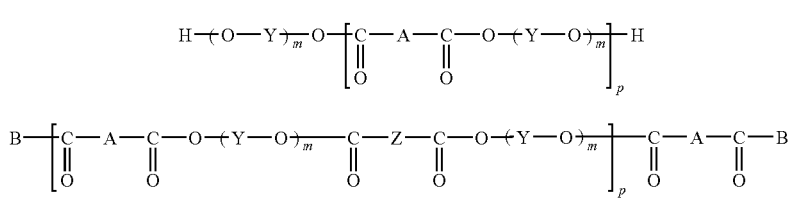

Formula (III-1)

Formula (III-2)

In Formulae (III-1) and (III-2), Y represents a divalent hydrocarbon group; Z represents a divalent hydrocarbon group; B and B' each independently represent —O—(Y—O)$_m$—H or —O—(Y—O)$_m$—CO- Z-CO—OR$_7$; R$_7$ represents a hydrogen atom, an alkyl group, a substituted or unsubstituted aryl group, a substituted or unsubstituted aralkyl group; m represents an integer from 1 to 5; p represents an integer from 5 to 5,000; and A represents a group represented by Formula (IV).

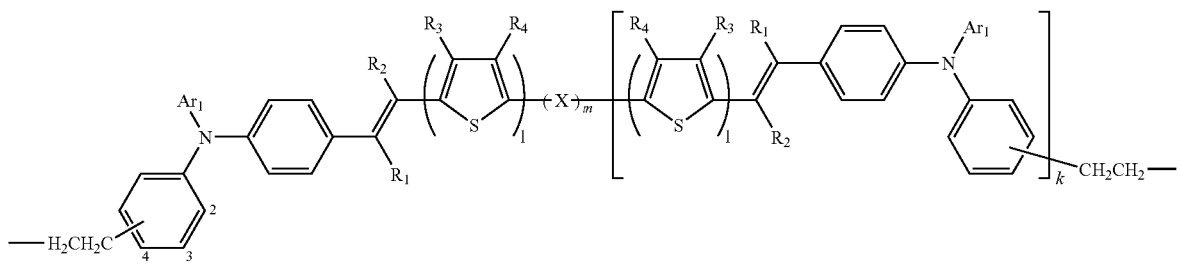

Formula (IV)

In Formula (IV), Ar$_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; R$_1$ to R$_4$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

In Formula (IV), X may represent a divalent straight-chain hydrocarbon group having 2 to 6 carbon atoms, a divalent branched-chain hydrocarbon group having 3 to 7 carbon atoms, a substituted or unsubstituted divalent polynuclear aromatic hydrocarbon having 1 to 8 aromatic rings, a substituted or unsubstituted divalent condensed aromatic hydrocarbon having 1 to 8 aromatic rings, or a substituted or unsubstituted divalent aromatic heterocyclic ring having 1 to 11 heterocyclic rings.

In Formula (IV), X may represent a group represented by one selected from the group consisting of Structural Formulae (II-1) to (II-5).

Structural Formula (II-1)

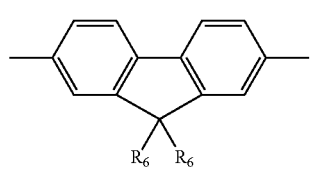

-continued

Structural Formula (II-2)

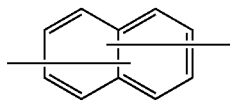

Structural Formula (II-3)

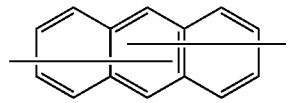

Structural Formula (II-4)

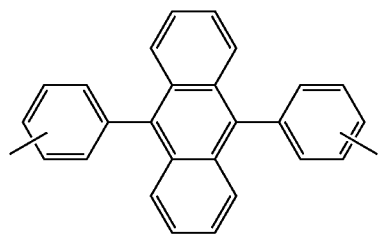

Structural Formula (II-5)

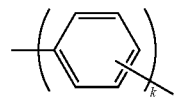

In Structural Formula (II-1), R$_6$ represents a hydrogen atom, an alkyl group, a substituted or unsubstituted aryl group, or a substituted or unsubstituted aralkyl group; and in Structural Formula (II-5), k represents an integer from 1 to 5.

In Formula (IV), Ar$_1$ may represent a substituted or unsubstituted phenyl group.

In Formula (IV), $Ar_1$ may represent a substituted or unsubstituted monovalent polynuclear aromatic hydrocarbon having 2 to 20 aromatic rings.

In Formula (IV), $Ar_1$ may represent a substituted or unsubstituted monovalent condensed aromatic hydrocarbon having 2 to 20 aromatic rings.

In Formula (IV), $Ar_1$ may represent a substituted or unsubstituted monovalent aromatic heterocyclic ring.

In Formula (IV), $Ar_1$ may represent a substituted or unsubstituted monovalent aromatic group containing at least one aromatic heterocyclic ring.

In Formulae (III-1) and (III-2), p may represent an integer from 10 to 1,000.

A weight-average molecular weight Mw of the polymer may be in a range of 10,000 to 300,000.

EXAMPLES

Hereinafter, the present invention will be described with reference to Examples, but it should be understood that the invention is not limited to the Examples.

Example 1

Acetanilide (25.0 g), methyl 4-iodophenylpropionate (64.4 g), potassium carbonate (38.3 g), copper sulfate pentahydrate (2.3 g), and n-tridecane (50 ml) are placed in a 500-ml three-necked flask and heated and stirred at 230° C. under nitrogen stream for 20 hours. After the termination of reaction, a solution of potassium hydroxide (15.6 g) in ethylene glycol (300 ml) is added thereto; the mixture is heated under reflux in a nitrogen stream for 3.5 hours and cooled to room temperature; and then, the reaction solution is poured in 1 L of distilled water, and the solution is neutralized with hydrochloric acid, to give a crystalline precipitate. The crystal is collected by filtration with suction, washed thoroughly with water, and transferred into a 1-L flask.

Toluene (500 ml) is added thereto; the mixture is heated under reflux while water is removed by azeotropic distillation; a solution containing conc. sulfuric acid (1.5 ml) in methanol (300 ml) is added thereto; and the mixture is heated under reflux in a nitrogen stream for 5 hours. After the reaction, the product is extracted with toluene, and the organic phase is washed thoroughly with distilled water. Then, the resultant is dried over anhydrous sodium sulfate; the solvent is removed under reduced pressure; and recrystallization from hexane gives 36.5 g of a diarylamine (DAA-1).

The DAA-1 (10.0 g) obtained, a monoiodo compound (13.4 g), potassium carbonate (8.1 g), copper sulfate pentahydrate (0.5 g), and o-dichlorobenzene (15 ml) are placed in a 200-ml three-necked flask and the mixture is heated under reflux in a nitrogen stream for 10 hours. After the termination of reaction, the solution is cooled to room temperature and dissolved in toluene (100 ml); insoluble matters are removed by Celite filtration; the filtrate is purified by silica gel column chromatography by using toluene, to give a compound 1 (7.4 g). The reaction formula is shown below. The melting point thereof is 143 to 145° C.

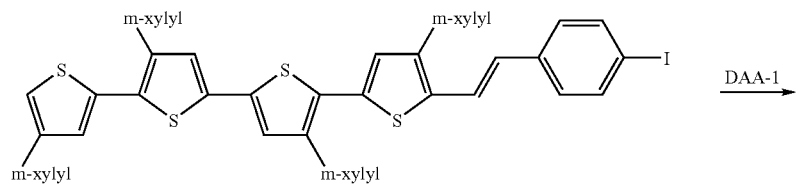

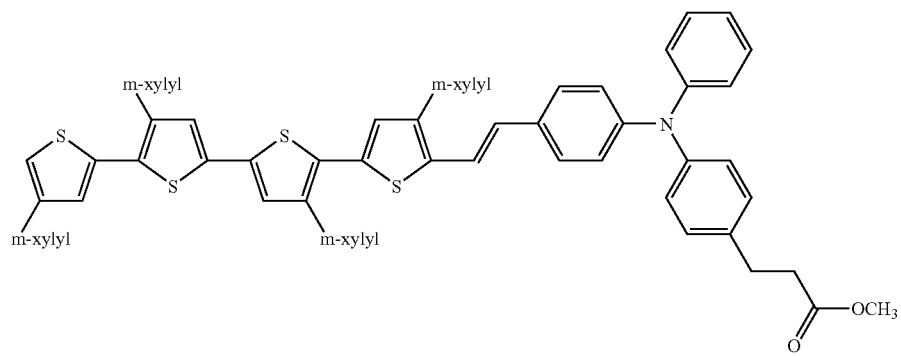

Compound 1

Example 2

4-Thienyl acetanilide (25.0 g), methyl 4-iodophenylpropionate (64.4 g), potassium carbonate (38.3 g), copper sulfate pentahydrate (2.3 g), and n-tridecane (50 ml) are placed in a 500-ml three-necked flask; and the mixture is heated under reflux at 230° C. in a nitrogen stream for 20 hours.

After the reaction, a solution of potassium hydroxide (15.6 g) in ethylene glycol (300 ml) is added thereto; the mixture is heated under reflux in a nitrogen stream for 3.5 hours, then cooled to room temperature, and poured into 1-L distilled water; and the mixture is neutralized with hydrochloric acid, to give a crystalline precipitate. The crystal is filtered, washed thoroughly with water, and transferred to a 1-L flask.

Toluene (500 ml) is added thereto; the mixture is heated under reflux while water is removed by azeotropic distillation; a solution containing conc. sulfuric acid (1.5 ml) in methanol (300 ml) is added thereto; and the mixture is heated under reflux in a nitrogen stream for 5 hours. After the reaction, the product is extracted with toluene, and the organic layer is washed thoroughly with distilled water.

Figure 1B:
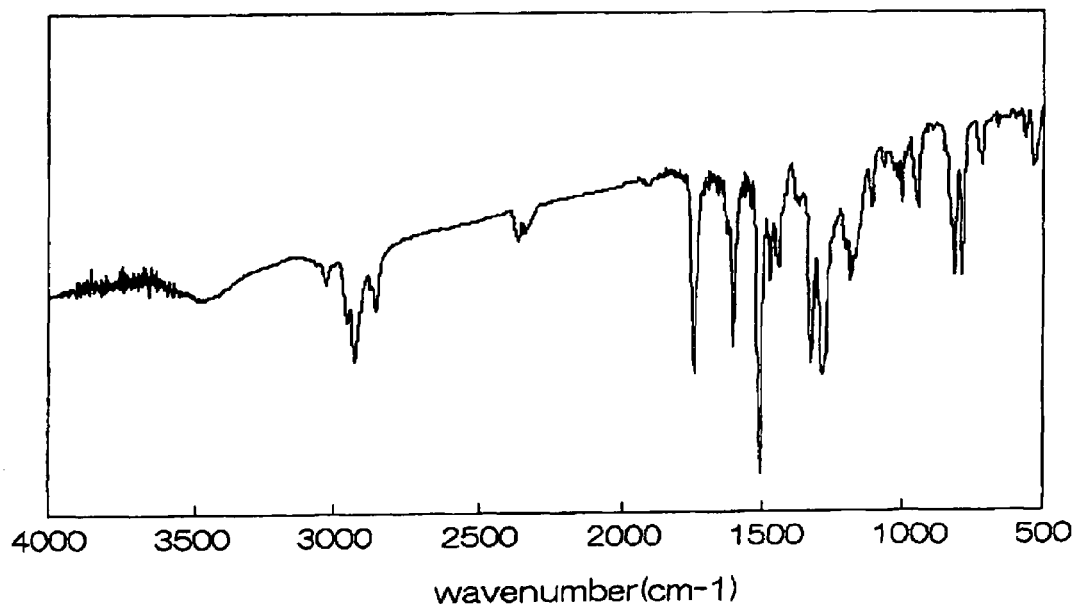
Figure 2A:
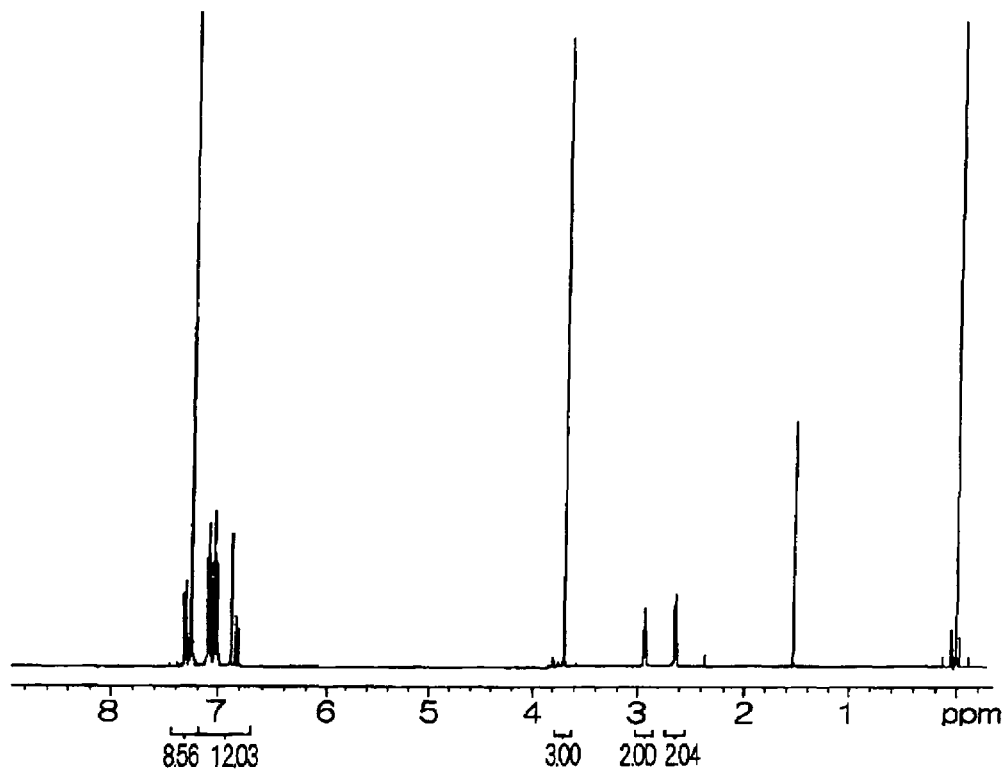
FIGS. 2A and 2B show measurement results, respectively NMR and IR spectra, of compound 5.
Figure 2B:
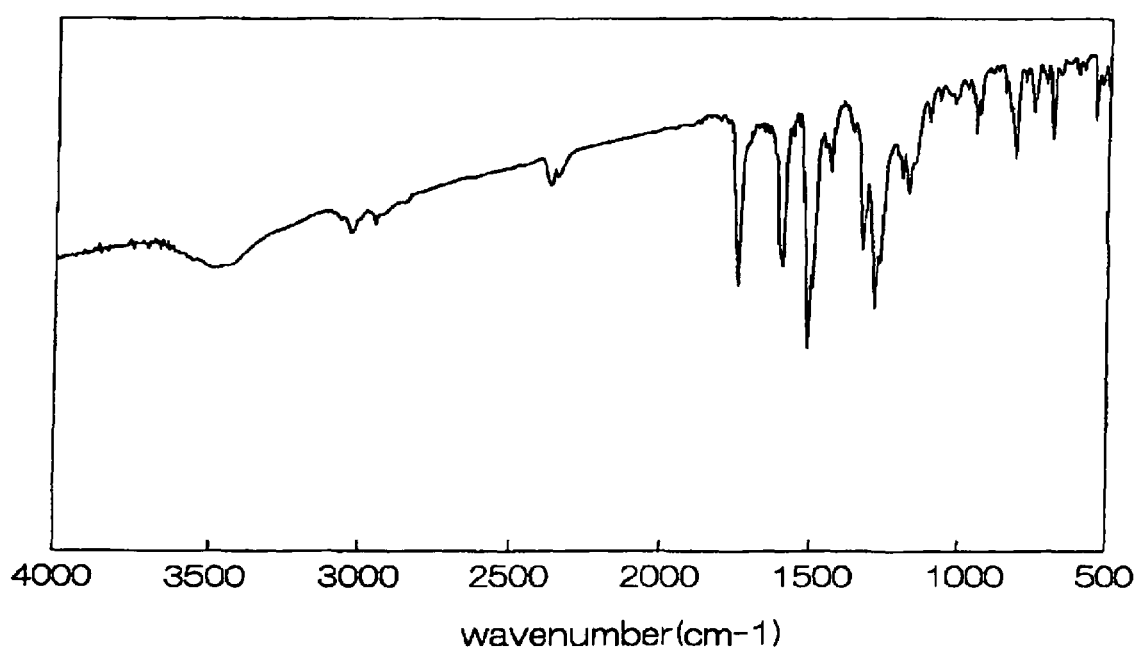
Figure 3A:
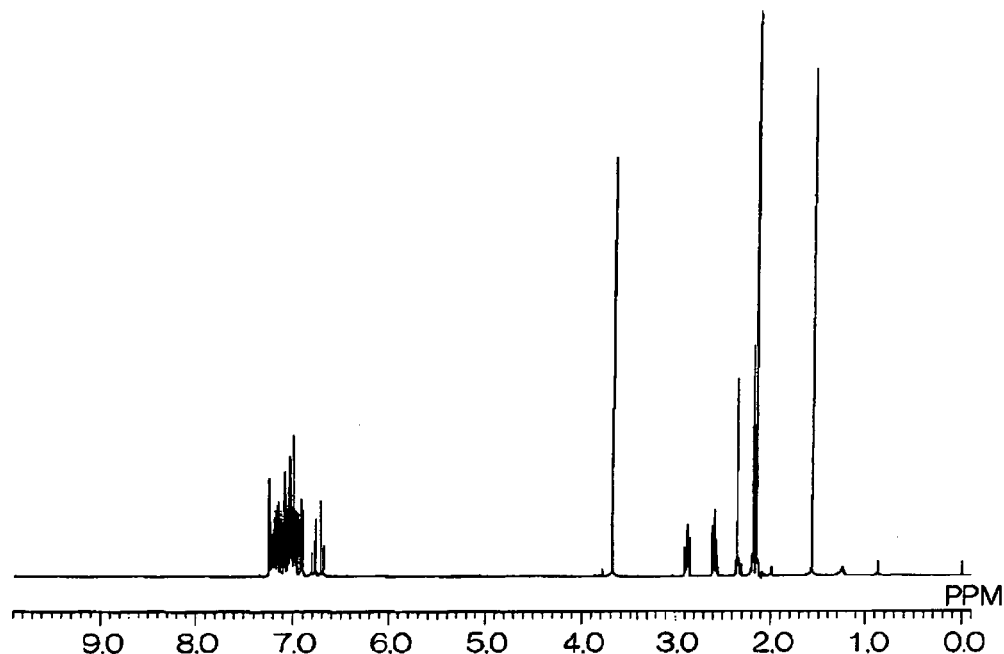
FIGS. 3A and 3B show measurement results, respectively NMR and IR spectra, of compound 7.
Figure 3B:
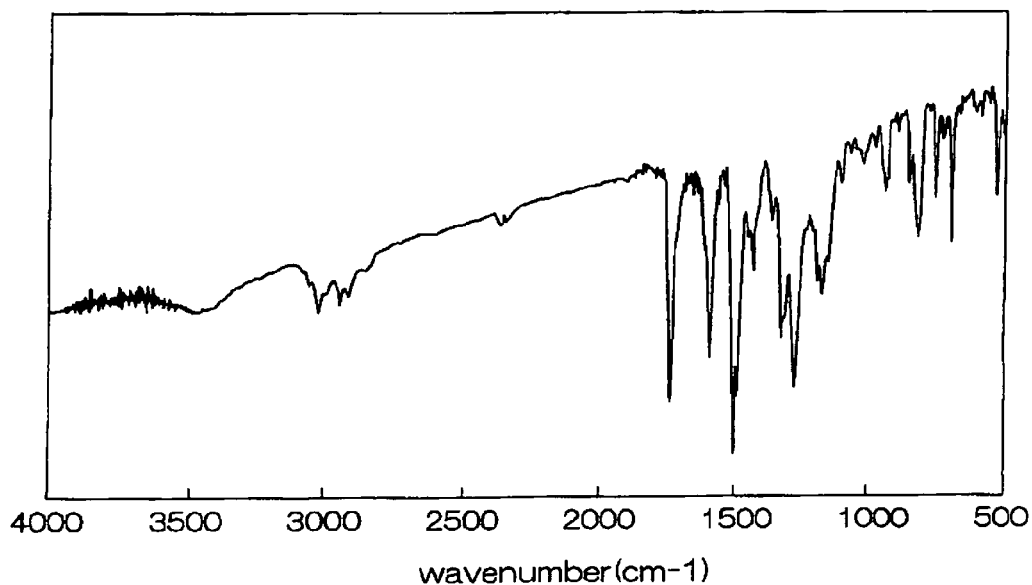

Then, the resultant is dried over anhydrous sodium sulfate; the solvent is removed under reduced pressure; and recrystallization from hexane gives 36.5 g of a diarylamine (DAA-2). The DAA-2 obtained (10.0 g), a monoiodo compound (13.4 g), potassium carbonate (8.1 g), copper sulfate pentahydrate (0.5 g), and o-dichlorobenzene (15 ml) are placed in a 200-ml three-necked flask and the mixture heated under reflux in a nitrogen stream for 10 hours. After the termination of reaction, the solution is cooled to room temperature and dissolved in toluene (100 ml); insoluble matters are removed by filtration; and the filtrate is purified by silica gel column chromatography by using toluene, to give a compound 2 (7.4 g). The reaction formula is shown below. The melting point thereof is 94 to 95° C. The NMR, and IR spectra thereof are shown in FIGS. 1A and 1B (FIGS. 1A, 2A, and 3A are NMR spectra, while FIGS. 1B, 2B and 3B are IR spectra).

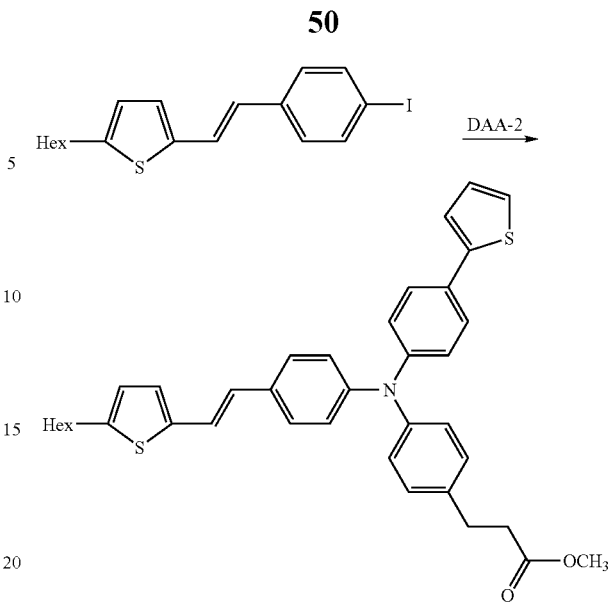

Compound 2

Example 3

The DAA-1 obtained in the same manner as in Example 1 (5.0 g), a diiodo compound (3.4 g), potassium carbonate (2.0 g), copper sulfate pentahydrate (0.2 g), and o-dichlorobenzene (10 ml) are placed in a 100-ml three-necked flask and the mixture is heated while stirred at 180° C. in a nitrogen stream for 10 hours. After the termination of reaction, the solution is cooled to room temperature and dissolved in toluene (100 ml); insoluble matters are removed by Celite filtration; and the filtrate is purified by silica gel column chromatography by using toluene, to give a compound 3 (4.8 g). The reaction formula is shown below. The melting point thereof is 223 to 226° C.

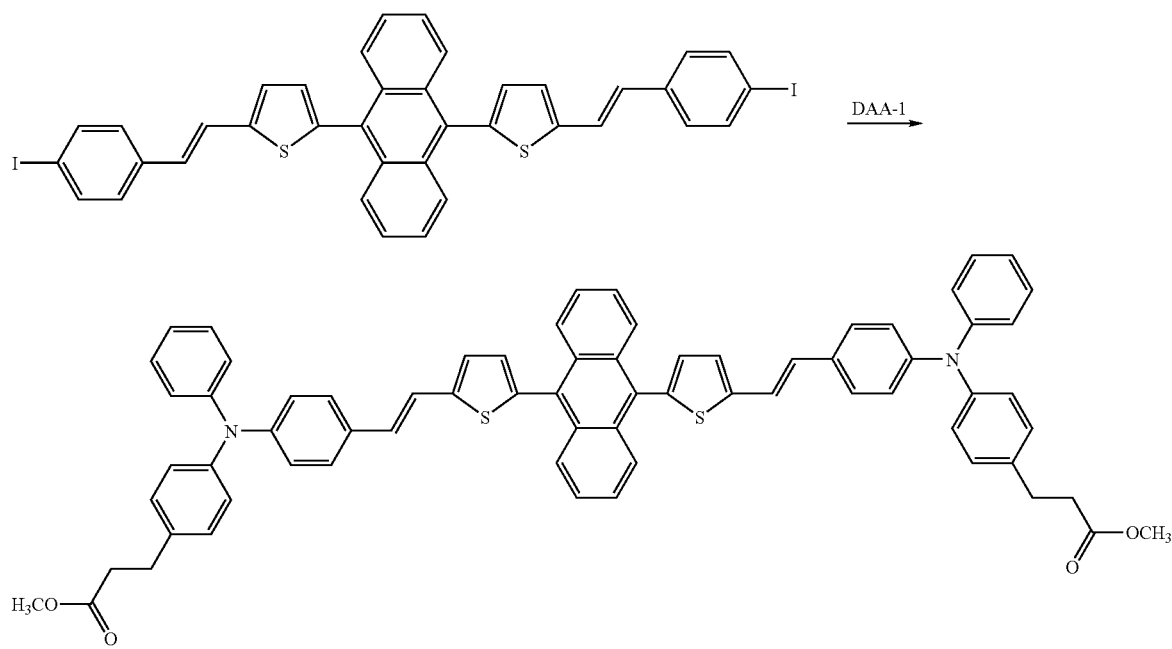

Compound 3

Example 4

The DAA-1 obtained in the same manner as in Example 1 (5.0 g), a diiodo compound (3.4 g), potassium carbonate (2.0 g), copper sulfate pentahydrate (0.2 g), and o-dichlorobenzene (10 ml) are placed in a 100-ml three-necked flask and the mixture is heated while stirred at 180° C. in a nitrogen stream for 10 hours. After the termination of reaction, the solution is cooled to room temperature and dissolved in toluene (100 ml); insoluble matters are removed by Celite filtration; and the filtrate is purified by silica gel column chromatography by using toluene, to give a compound 4 (4.8 g). The reaction formula is shown below. The melting point thereof is 232 to 234° C.

Compound 4

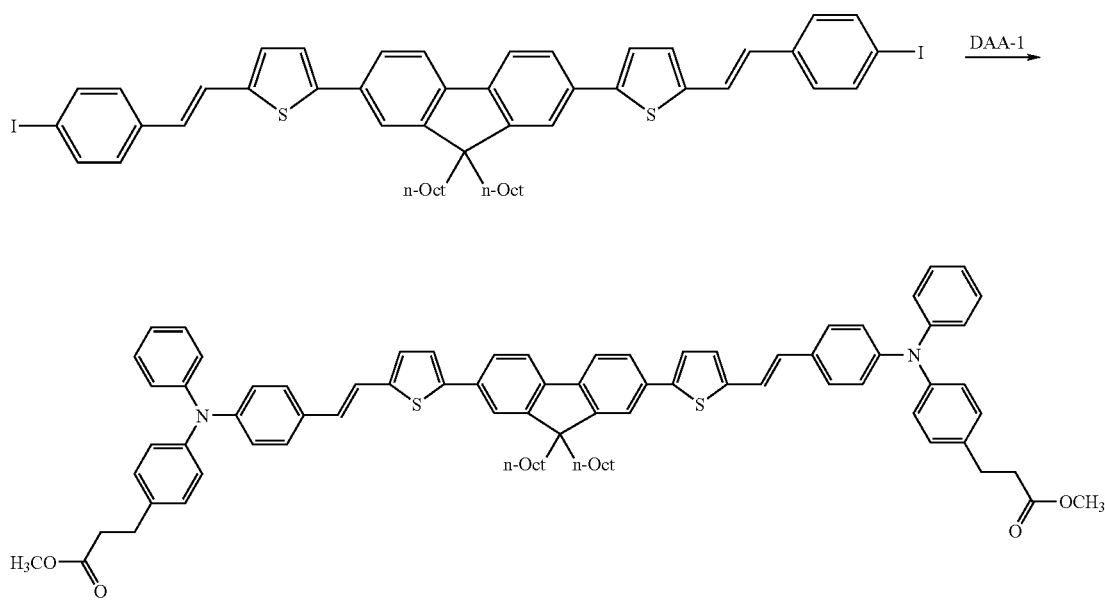

Example 5

DAA-1 (6.0 g), a diiodo compound (5.7 g), potassium carbonate (3.4 g), copper sulfate pentahydrate (0.2 g), and o-dichlorobenzene (15 ml) are placed in a 100-ml three-necked flask and the mixture is heated under reflux in a nitrogen stream for 9.5 hours. After the termination of reaction, the solution is cooled to room temperature and dissolved in toluene (100 ml); insoluble matters are removed by filtration; and the filtrate is purified by silica gel column chromatography by using toluene, to give a compound 5 (6.4 g). The melting point thereof is 164 to 166° C. The NMR and IR spectra are shown in FIGS. 2A and 2B.

Compound 5

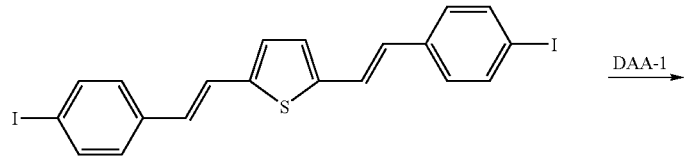

-continued

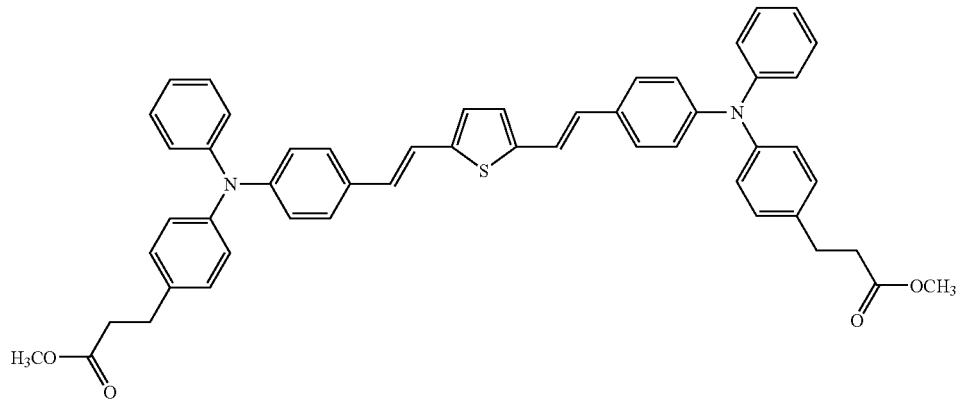

Example 6

The DAA-1 obtained in the same manner as in Example 1 (5.0 g), a diiodo compound (3.4 g), potassium carbonate (2.0 g), copper sulfate pentahydrate (0.2 g), and o-dichlorobenzene (10 ml) are placed in a 100-ml three-necked flask and the mixture is heated while stirred at 180° C. in a nitrogen stream for 10 hours. After the termination of reaction, the solution is cooled to room temperature and dissolved in toluene (100 ml); insoluble matters are removed by Celite filtration; and the filtrate is purified by silica gel column chromatography by using toluene, to give a compound 6 (4.8 g). The reaction formula is shown below. The melting point thereof is 202 to 204° C.

Example 7

The DAA-1 obtained in the same manner as in Example 1 (5.0 g), a diiodo compound (3.4 g), potassium carbonate (2.0 g), copper sulfate pentahydrate (0.2 g), and o-dichlorobenzene (10 ml) are placed in a 100-ml three-necked flask and the mixture is heated while stirred at 180° C. under nitrogen stream for 10 hours. After the termination of reaction, the solution is cooled to room temperature and dissolved in toluene (100 ml); insoluble matters are removed by Celite filtration; and the filtrate is purified by silica gel column chromatography by using toluene, to give a compound 7 (4.8 g). The reaction formula is shown below. The melting point thereof is 150 to 152° C. The NMR, and IR spectra are shown in FIGS. 3A and 3B.

Compound 6

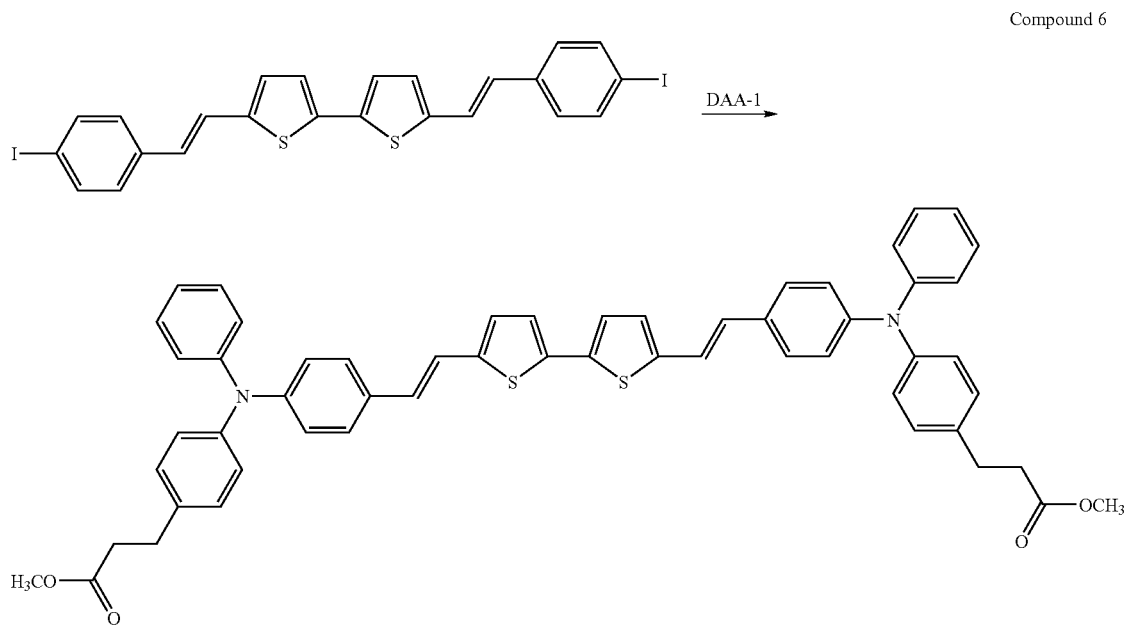

Compound 7

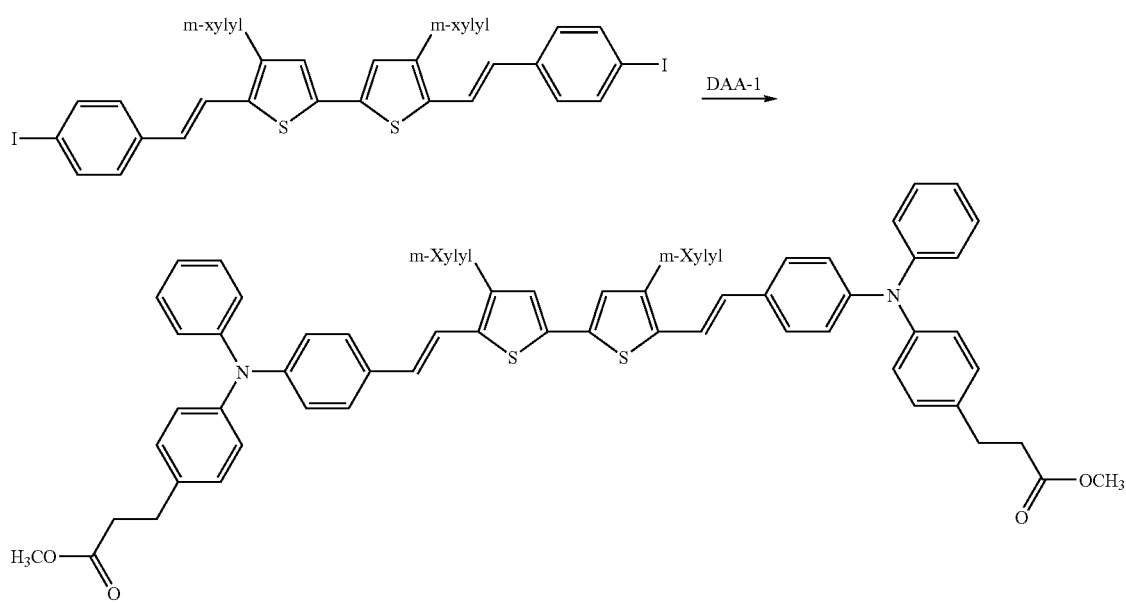

Example 8

The DAA-1 obtained in the same manner as in Example 1 (5.0 g), a monoiodo compound (3.4 g), potassium carbonate (2.0 g), copper sulfate pentahydrate (0.2 g), and o-dichlorobenzene (10 ml) are placed in a 100-ml three-necked flask and the mixture is heated while stirred at 180° C. under nitrogen stream for 10 hours. After the termination of reaction, the solution is cooled to room temperature and dissolved in toluene (100 ml); insoluble matters are removed by Celite filtration; and the filtrate is purified by silica gel column chromatography by using toluene, to give 4.8 g of a chlorinated compound of triarylamine (TAA-Cl-1). Then, under nitrogen stream, anhydrous nickel chloride (1.0 g), triphenylphosphine (7.9 g), and anhydrous DMF (40 ml) are placed in a 100 ml three-necked flask and the mixture is stirred under heat. Zinc powder (0.5 g) is added to the reaction solution when the temperature of the reaction solution becomes 50° C., and the mixture is stirred under heat at 50° C. for 1 hour. Then, TAA-Cl-1 (4.0 g) is added thereto, and the mixture is stirred under heat at 50° C. for 0.5 hour. After the termination of reaction, the mixture is cooled to room temperature, poured into 400 ml of distilled water, and stirred thoroughly. The crystalline precipitate is collected by filtration with suction and washed with distilled water, to give a crude product. The crude product is purified by silica gel column chromatography by using hexane/ethyl acetate, to give a compound 8 (4.8 g). The reaction formula is shown below. The melting point thereof is 178 to 180° C.

Compound 8

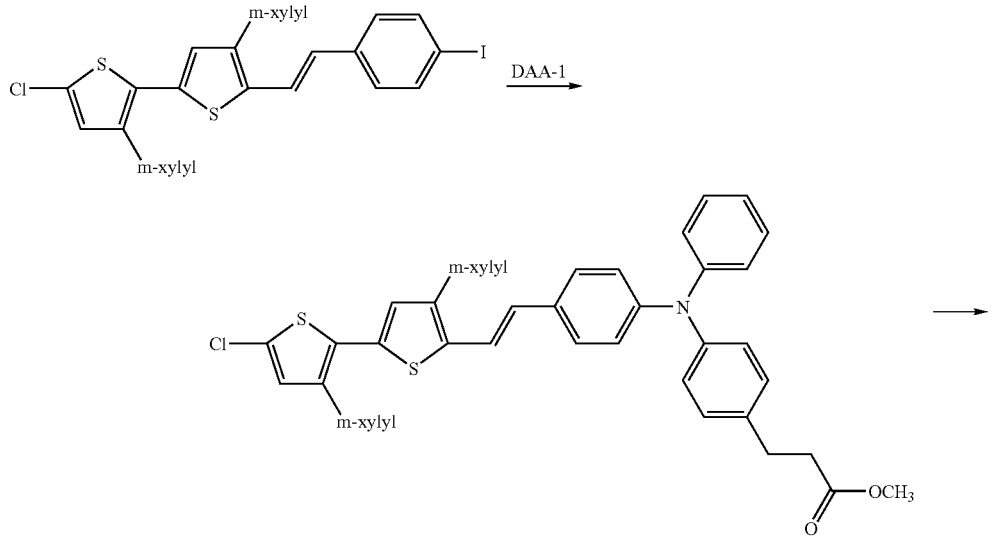

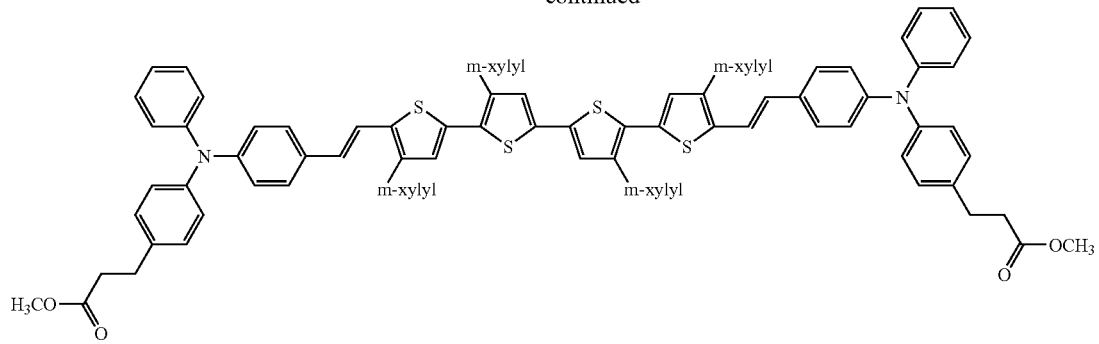

Example 9

4-Thienyl acetanilide (25.0 g), methyl 4-iodophenylpropionate (64.4 g), potassium carbonate (38.3 g), copper sulfate pentahydrate (2.3 g), and n-tridecane (50 ml) are placed in a 500-ml three-necked flask and the mixture is heated while stirred at 230° C. under nitrogen stream for 20 hours. After the reaction, a solution of potassium hydroxide (15.6 g) in ethylene glycol (300 ml) is added thereto; the mixture is heated under reflux in a nitrogen stream for 3.5 hours, then cooled to room temperature, and poured into 1-L distilled water; and the mixture is neutralized with hydrochloric acid, to give a crystalline precipitate. The precipitate is collected by filtration, washed thoroughly with water, and transferred to a 1-L flask. Toluene (500 ml) is added thereto; the mixture is heated under reflux while water is removed by azeotropic distillation; a solution of conc. sulfuric acid (1.5 ml) in methanol (300 ml) is added thereto; and the mixture is heated under reflux in a nitrogen stream for 5 hours. After the reaction, the product is extracted with toluene, and the organic layer is washed thoroughly with distilled water. Then, the resultant is dried over anhydrous sodium sulfate; the solvent is removed under reduced pressure; and recrystallization from hexane gives 36.5 g of a diarylamine (DAA-2). The DAA-2 obtained (10.0 g), a duiodo compound (13.4 g), potassium carbonate (8.1 g), copper sulfate pentahydrate (0.5 g), and o-dichlorobenzene (15 ml) are placed in a 200-ml three-necked flask and the mixture is heated under reflux in a nitrogen stream for 10 hours. After the termination of reaction, the solution is cooled to room temperature and dissolved in toluene (100 ml); insoluble matters are removed by filtration; and the filtrate is purified by silica gel column chromatography by using toluene, to give a compound 9 (7.4 g). The reaction formula is shown below. The melting point thereof is 100 to 103° C.

Compound 9

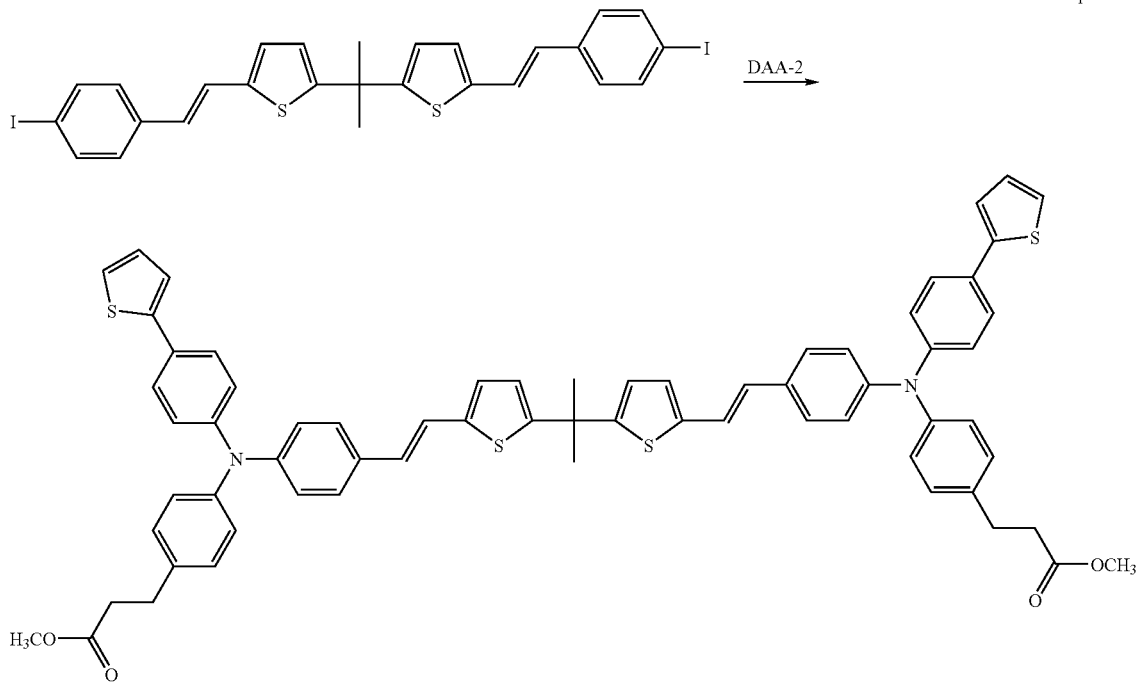

Example 10

The diamine (compound 3) obtained in Example 3 (1.0 g), ethylene glycol (10.0 ml) and tetrabutoxytitanium (0.02 g) are placed in a 50-ml three-necked round-bottomed flask and the mixture is stirred at 200° C. under heat in a nitrogen stream for 6.5 hours. After confirmation by TLC that the raw diamine is consumed completely, the mixture is allowed to react at 210° C. additionally for four hours at a reduced pressure of 0.5 mm Hg while ethylene glycol is distilled off. Then, the mixture after cooled to room temperature is dissolved in 50 ml of monochlorobenzene; insoluble matters are removed by filtration with a polytetrafluoroethylene (PTFE) filter having a 0.5-μm pore; and the filtrate is added dropwise to 500 ml of stirred methanol, to give a polymer precipitate. The polymer obtained is filtered, washed thoroughly with methanol, and dried, to give 1.0 g of a polymer (compound 10). The molecular weight Mw of the polymer, as determined by gel-permeation chromatography (GPC), is $3.68 \times 10^4$ (as styrene); the Mn/Mw is 2.62; and the polymerization degree p, as determined from the molecular weight of its monomers, is approximately 34.

Example 11

The diamine (compound 4) obtained in Example 4 (1.0 g), ethylene glycol (8.0 ml) and tetrabutoxytitanium 0.02 g are placed in a 50-ml three-necked round-bottomed flask and the mixture is heated while stirred at 200° C. under nitrogen stream for 7 hours. After confirmation by TLC that the raw diamine is consumed completely, the mixture is allowed to react at 210° C. additionally for five hours at a reduced pressure of 0.5 mm Hg while ethylene glycol is distilled off. Then, the mixture after cooled to room temperature is dissolved in 50 ml of monochlorobenzene; insoluble matters are removed by filtration with a polytetrafluoroethylene (PTFE) filter having a 0.5-μm pore; and the filtrate is added dropwise to 500 ml of stirred methanol, to give a polymer precipitate. The polymer obtained is filtered, washed thoroughly with methanol, and dried to give 0.9 g of a polymer (compound 11). The molecular weight Mw of the polymer, as determined by GPC, is $8.56 \times 10^4$ (as styrene); the Mn/Mw is 3.24; and the polymerization degree p, as determined from the molecular weight of its monomers, is approximately 86.

Example 12

The diamine (compound 5) obtained in Example 5 (0.8 g), ethylene glycol (8.0 ml) and tetrabutoxytitanium (0.02 g) are placed in a 50-ml three-necked round-bottomed flask and the mixture is heated while stirred at 200° C. under nitrogen stream for 8 hours. After confirmation by TLC that the raw diamine is consumed completely, the mixture is allowed to react at 200° C. additionally for four hours at a reduced pressure of 0.5 mm Hg while ethylene glycol is distilled off. Then, the mixture after cooled to room temperature is dissolved in 50 ml of monochlorobenzene; insoluble matters are removed by filtration with a polytetrafluoroethylene (PTFE) filter having a 0. 5-μm pore; and the filtrate is added dropwise to 500 ml of stirred methanol, to give a polymer precipitate. The polymer obtained is filtered, washed thoroughly with methanol, and dried, to give 0.9 g of a polymer (compound 12). The molecular weight Mw of the polymer, as determined by GPC, is $8.23 \times 10^4$ (as styrene); the Mn/Mw is 4.34; and the polymerization degree p, as determined from the molecular weight of its monomers, is approximately 64.

Example 13

The diamine (compound 6) obtained in Example 6 (0.7 g), ethylene glycol (8.5 ml) and tetrabutoxytitanium (0.02 g) are placed in a 50-ml three-necked round-bottomed flask and the mixture is heated while stirred at 200° C. under nitrogen stream for 5 hours. After confirmation by TLC that the raw diamine is consumed the mixture is allowed to react at 210° C. additionally for four hours at a reduced pressure of 0.5 mm Hg while ethylene glycol is distilled off Then, the mixture after cooled to room temperature is dissolved in 50 ml of monochlorobenzene; insoluble matters are removed by filtration with a polytetrafluoroethylene (PTFE) filter having a 0.5-μm pore; and the filtrate is added dropwise to 500 ml of stirred methanol, to give a polymer precipitate. The polymer obtained is filtered, washed thoroughly with methanol, and dried to give 0.6 g of a polymer (compound 13). The molecular weight Mw of the polymer, as determined by GPC, is $1.15 \times 10^5$ (as styrene); the Mw/Mn is 3.60; and the polymerization degree p, as determined from the molecular weight of its monomers, is approximately 120.

Example 14

The diamine (compound 7) obtained in Example 7 (0.8 g), ethylene glycol (8.0 ml) and tetrabutoxytitanium (0.02 g) are placed in a 50-ml three-necked round-bottomed flask and the mixture is heated while stirred at 200° C. under nitrogen stream for 5 hours. After confirmation by TLC that the raw diamine is consumed, the mixture is allowed to react at 210° C. additionally for four hours at a reduced pressure of 0.5 mm Hg while ethylene glycol is distilled off. Then, the mixture after cooled to room temperature is dissolved in 40 ml of monochlorobenzene; insoluble matters are removed by filtration with a polytetrafluoroethylene (PTFE) filter having a 0.5-μm pore; and the filtrate is added dropwise to 500 ml of stirred methanol, to give a polymer precipitate. The polymer obtained is filtered, washed thoroughly with methanol, and dried, to give 0.65 g of a polymer (compound 14). The molecular weight Mw of the polymer, as determined by GPC, is $9.56 \times 10^4$ (as styrene); the Mw/Mn is 2.65; and the polymerization degree p, as determined from the molecular weight of its monomers, is approximately 95.

Example 15

The diamine (compound 8) obtained in Example 8 (2.0 g), ethylene glycol (15 ml) and tetrabutoxytitanium (0.04 g) are placed in a 50-ml three-necked round-bottomed flask and the mixture is heated while stirred at 200° C. under nitrogen stream for 8 hours. After confirmation by TLC that the raw diamine is consumed completely, the mixture is allowed to react at 230° C. additionally for five hours at a reduced pressure of 0.5 mm Hg while ethylene glycol is distilled off. Then, the mixture after cooled to room temperature is dissolved in 100 ml of monochlorobenzene; insoluble matters are removed by filtration with a polytetrafluoroethylene (PTFE) filter having a 0.5-μm pore; and the filtrate is added dropwise to 1 L of stirred methanol, to give a polymer precipitate. The polymer obtained is filtered, washed thoroughly with methanol, and dried to give 1.9 g of a polymer (compound 15). The molecular weight Mw of the polymer, as determined by GPC, is $6.85 \times 10^4$ (as styrene); the Mw/Mn is 3.64; and the polymerization degree p, as determined from the molecular weight of its monomers, is approximately 68.

Comparative Example 1

For comparison with the thiophene-containing compounds and the thiophene-containing compound polymers according to the present invention obtained in the Examples above, MEH-PPV (poly[2-methoxy-5-(2'-ethylhexyloxy)-1,4-phenylenevinylene], weight-average molecular weight: 86,000) is prepared and used as a Comparative Example.

The mobility and the glass transition temperature of the thiophene-containing compounds and the polymers obtained in the Examples and the sample of Comparative Example 1 are determined respectively by a Time-of-Flight method and a differential scanning calorimetry (DSC) (Tg/DTA 6200, manufacture by Seiko Instruments). In addition, the absorption spectrum thereof is determined by using an ultraviolet-visible absorption spectrophotometer (U-4000, manufactured by Hitachi); and the emission spectrum, by using a He—Cd laser (excitation wavelength: 325 nm) (DAM-11, manufactured by Hamamatsu Photonics). Results are summarized in the following Table 10.

TABLE 10

| | Mobility ($cm^2$/Vs) | Absorption wavelength λmax (nm) | Emission wavelength λmax (nm) | Glass transition temperature (° C.) |
|---|---|---|---|---|
| Compound of Example 1 | $2.0 \times 10^{-6}$ | 345 | 425 | 6 |
| Compound of Example 2 | $1.5 \times 10^{-6}$ | 380 | 460 | 10 |
| Compound of Example 3 | $5.5 \times 10^{-6}$ | 485 | 430 | 36 |
| Compound of Example 4 | $6.5 \times 10^{-6}$ | 439 | 497 | 38 |
| Compound of Example 5 | $1.0 \times 10^{-6}$ | 420 | 495 | 54 |
| Compound of Example 6 | $2.5 \times 10^{-7}$ | 460 | 565 | 77 |
| Compound of Example 7 | $5.5 \times 10^{-6}$ | 470 | 546 | 86 |
| Compound of Example 8 | $2.0 \times 10^{-6}$ | 432 | 490 | 72 |
| Compound of Example 9 | $1.0 \times 10^{-6}$ | 370 | 452 | 53 |
| Polymer of Example 14 | $2.3 \times 10^{-5}$ | 472 | 550 | 121 |
| Comparative Example 1 (MEH-PPV) | $10^{-8} \sim 10^{-7}$ | 479 | 550 | 75 |

The results in Table 10 demonstrate that each of the thiophene-containing compounds according to an aspect of the invention and the polymers thereof has high mobility and favorable light-emitting characteristics.

Detailed reaction formulae for preparation of the compounds 1 to 9 respectively in Examples 1 to 9 are shown below.

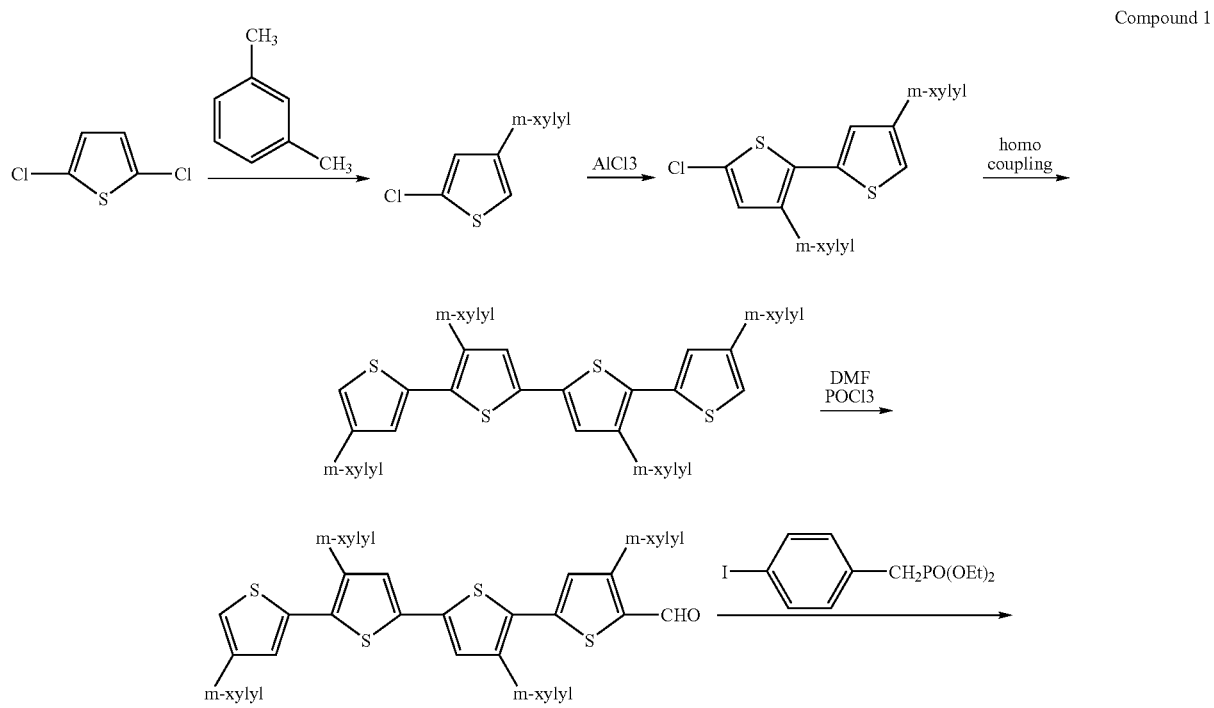

Compound 1

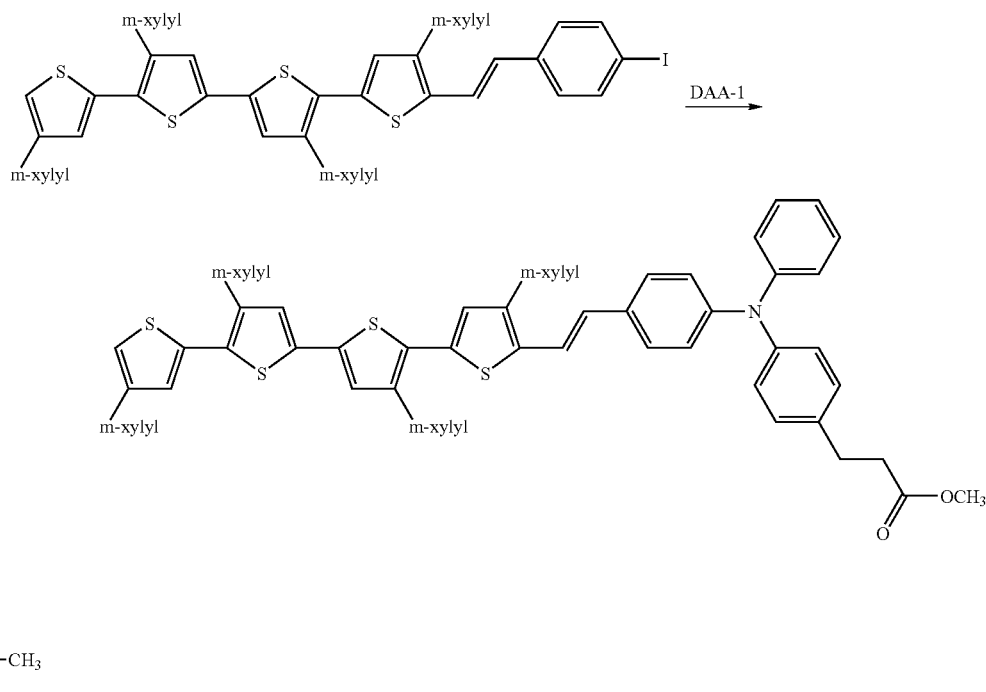
Compound 2
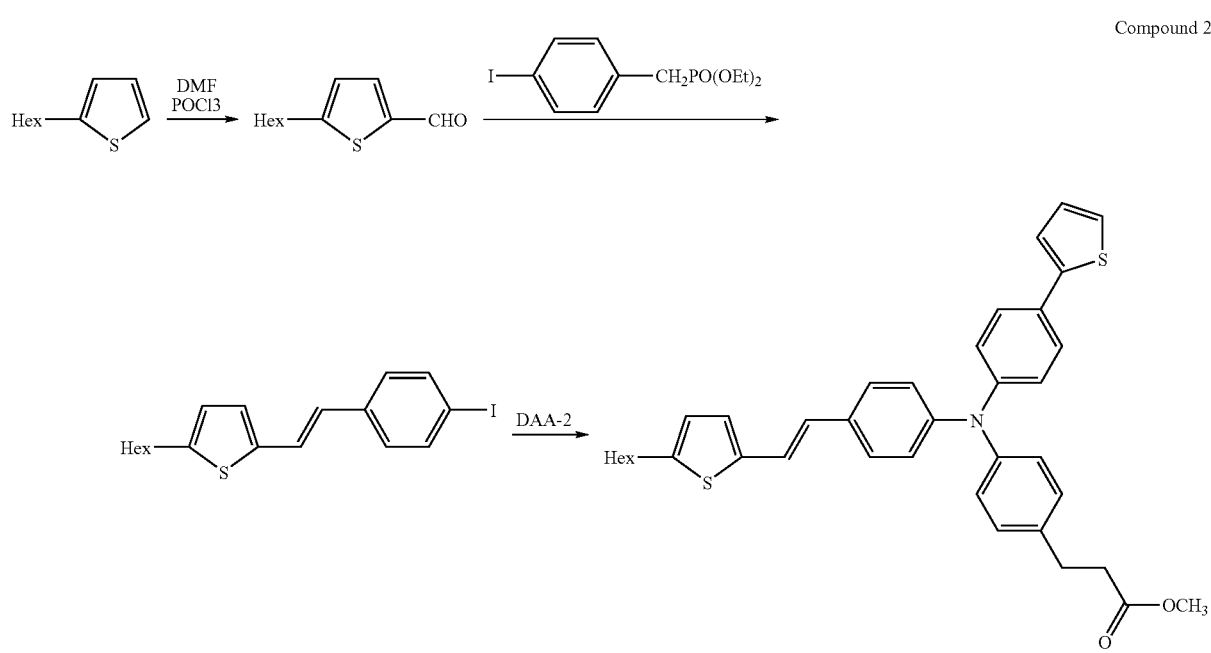
Compound 3
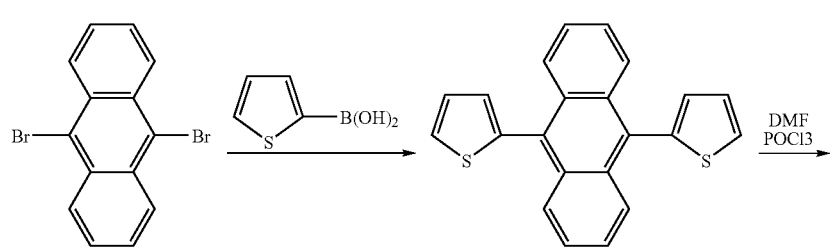

-continued
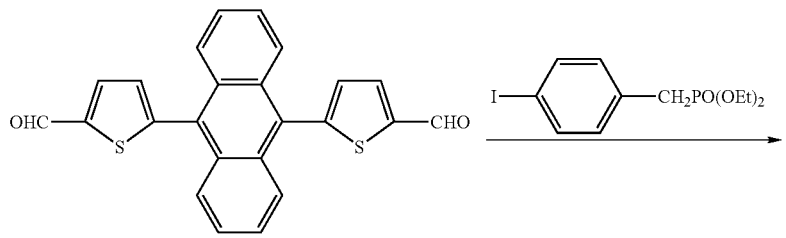
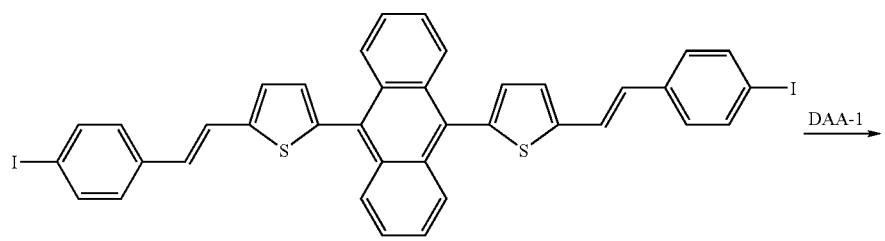
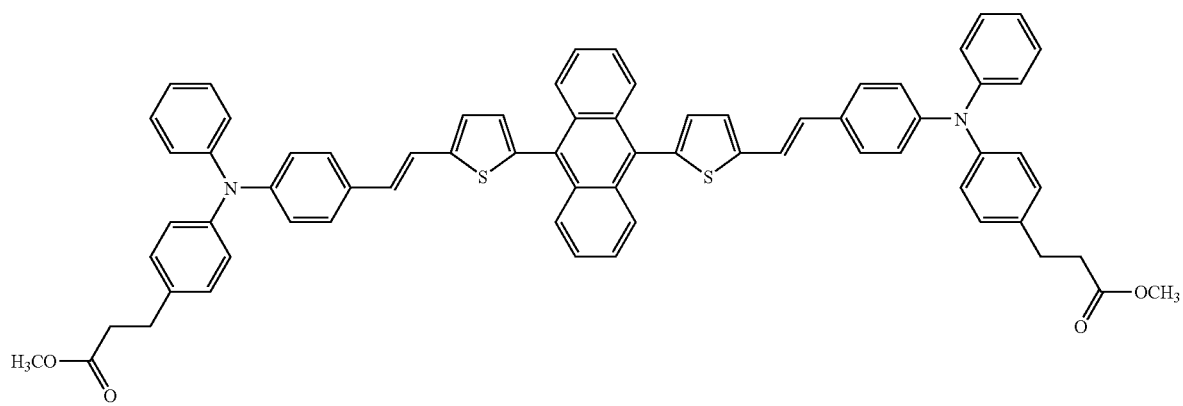
Compound 4
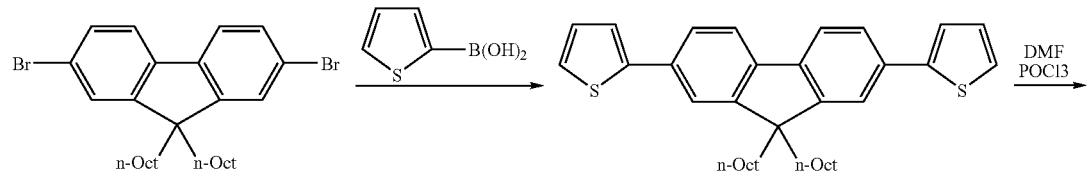
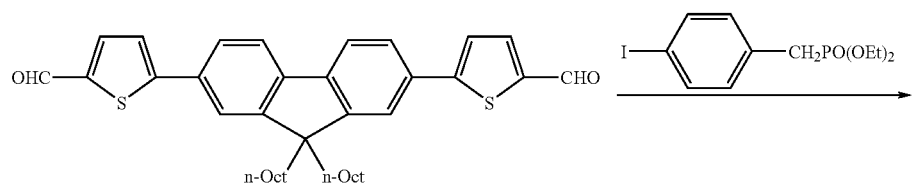
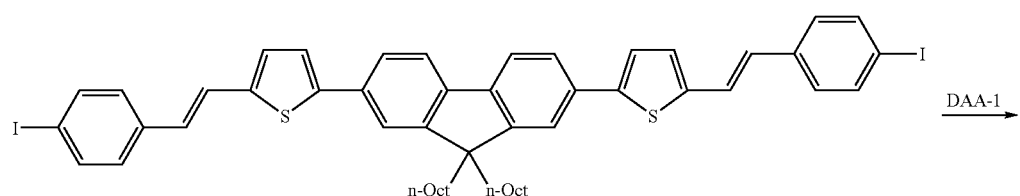

-continued
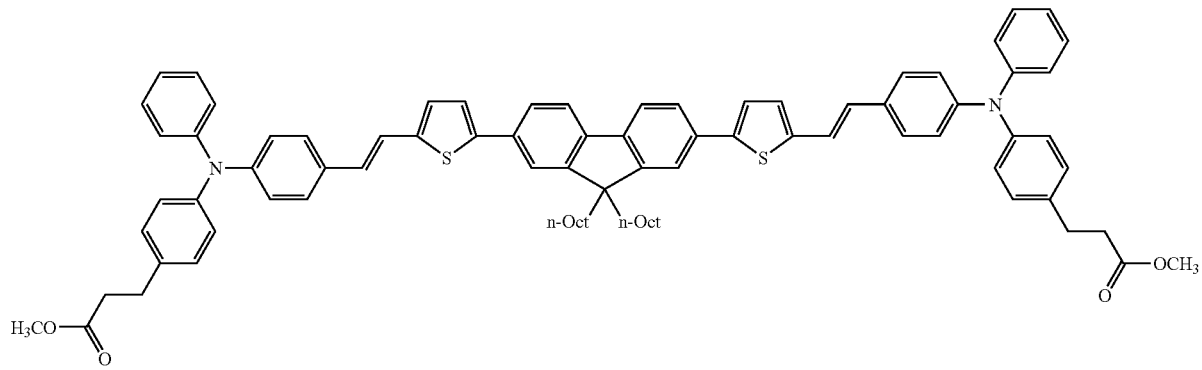
Compound 5
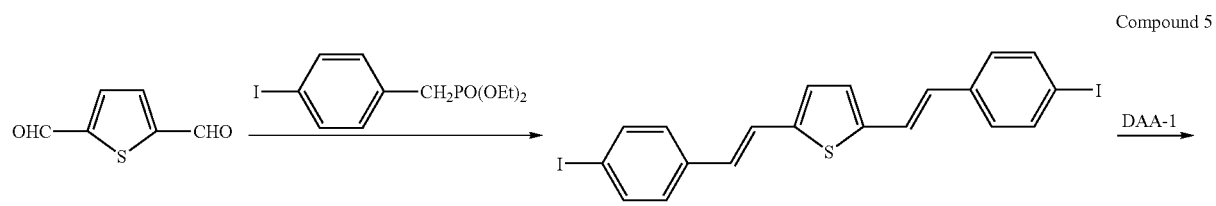
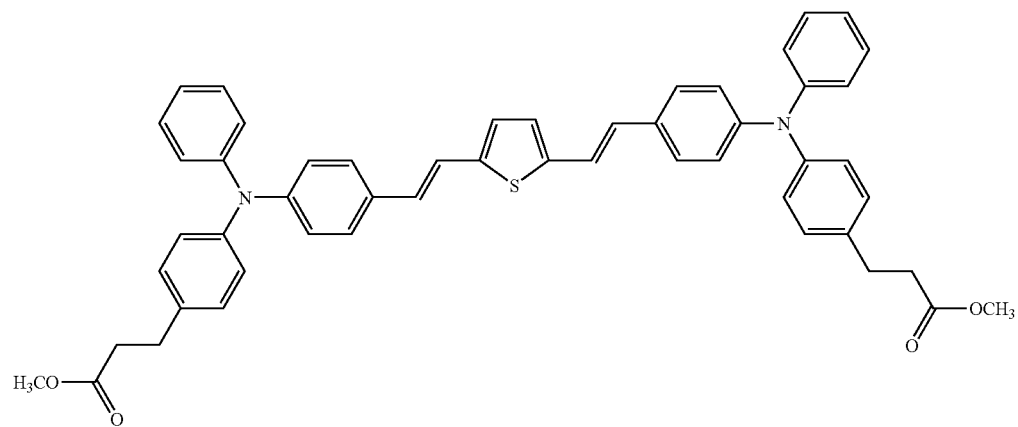
Compound 6
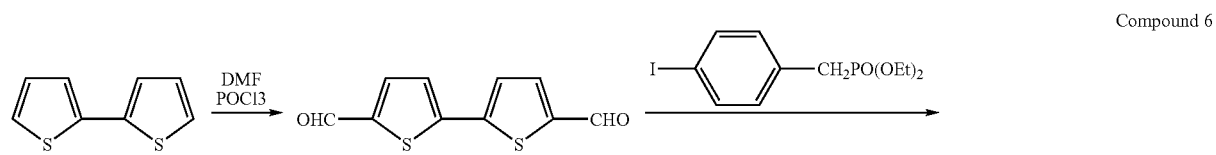
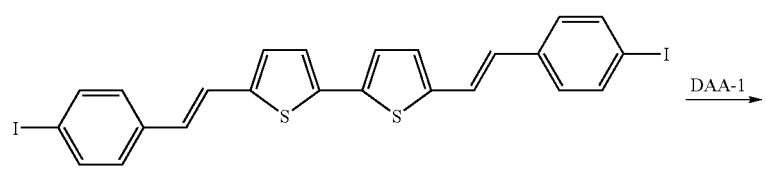

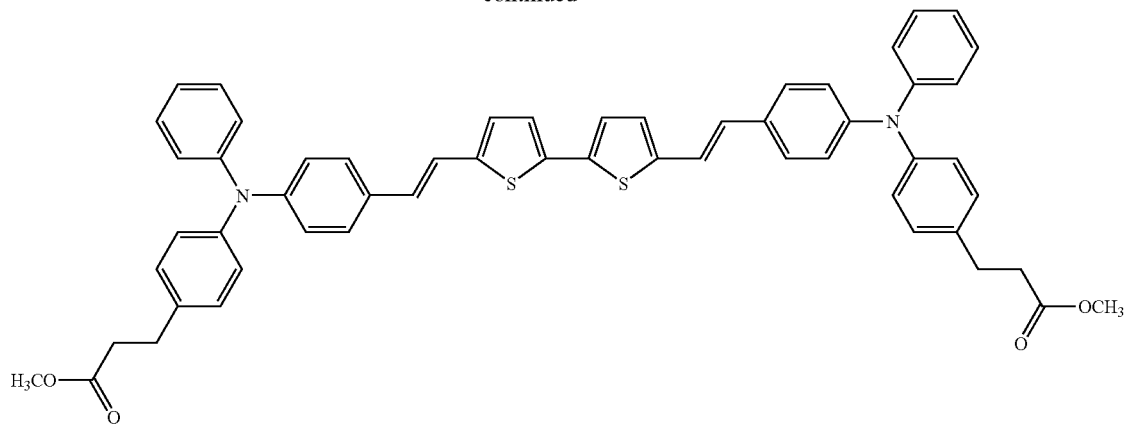
Compound 7
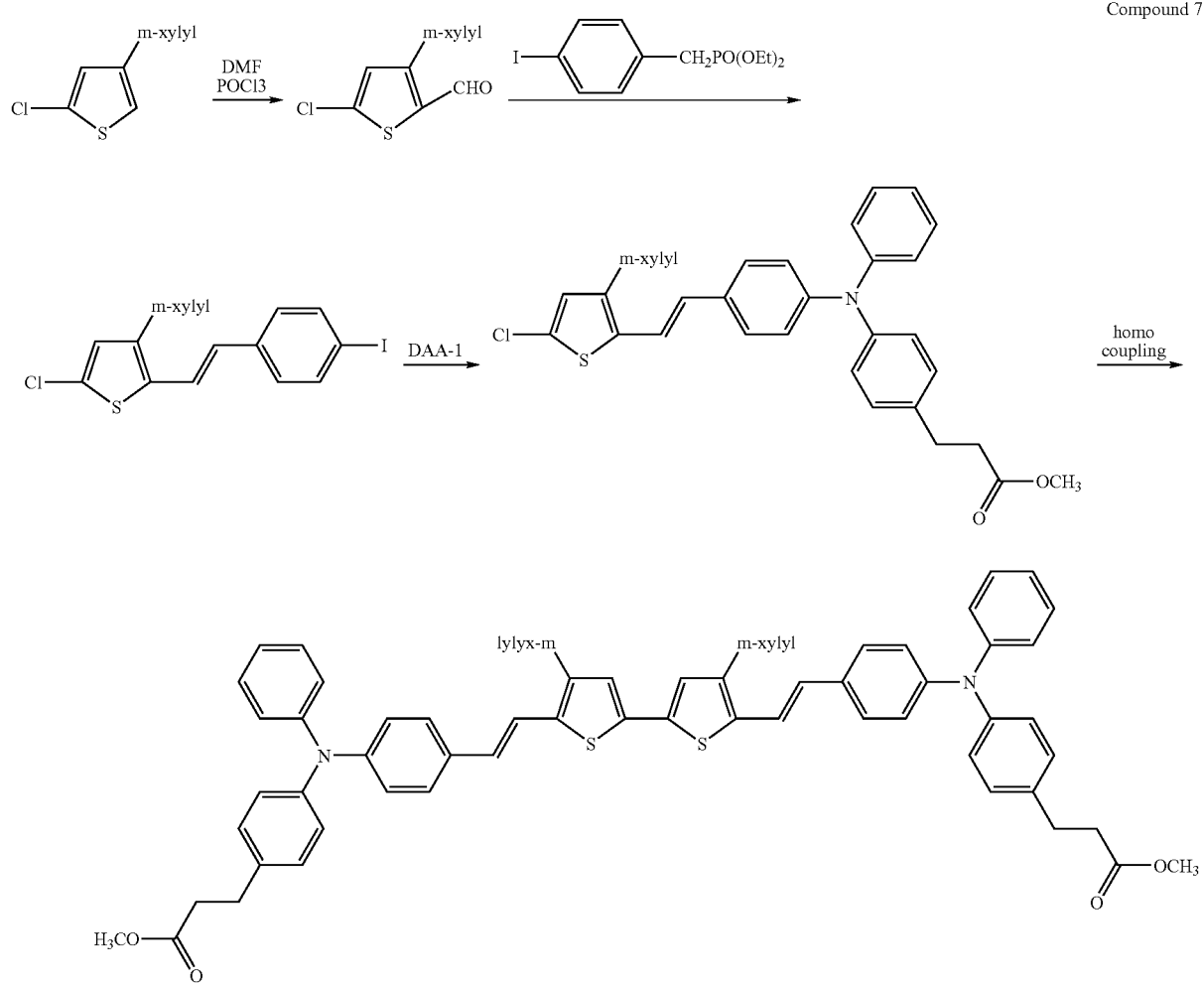
Compound 8
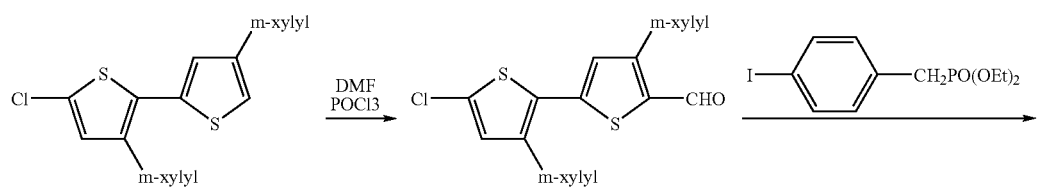

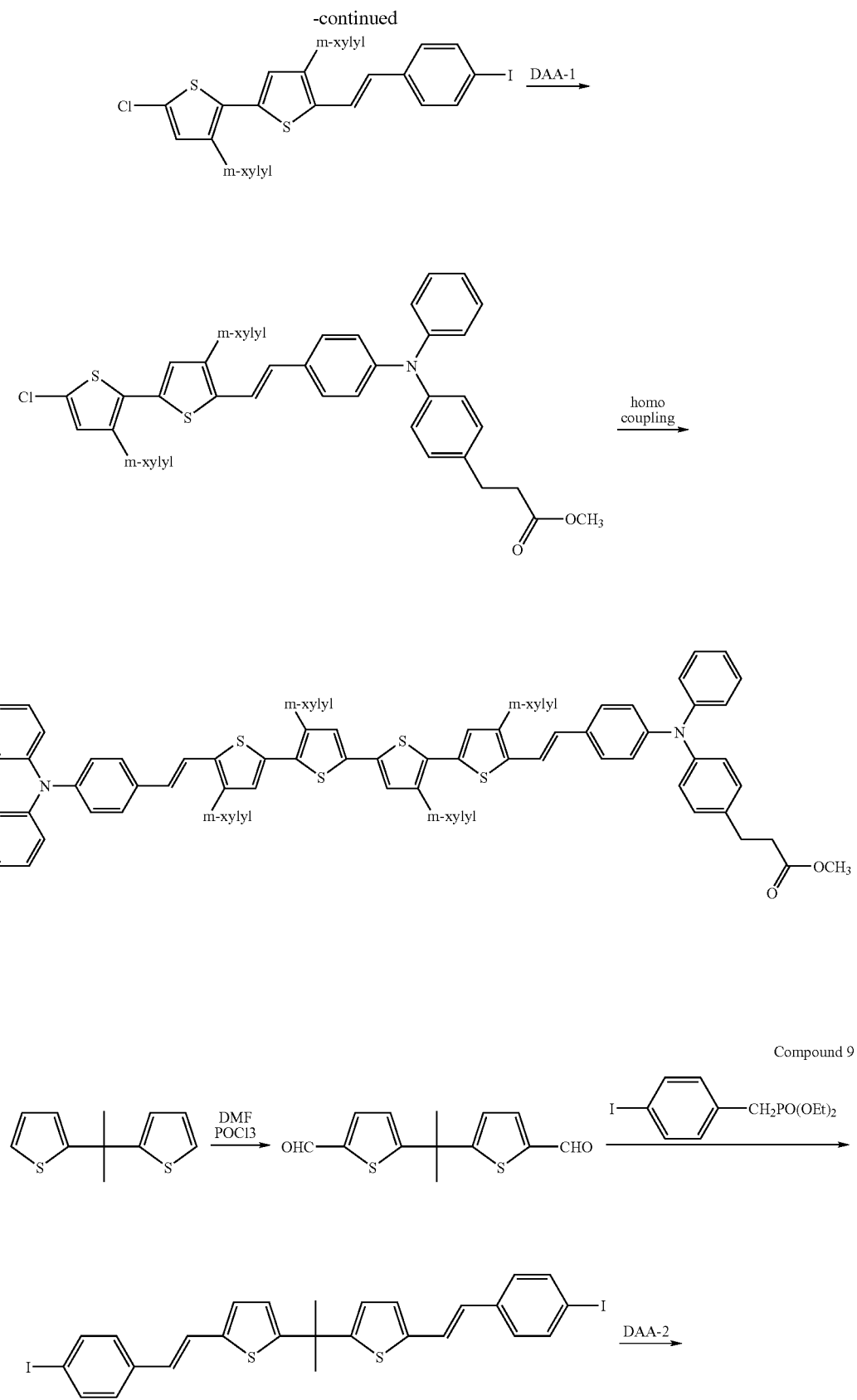

-continued

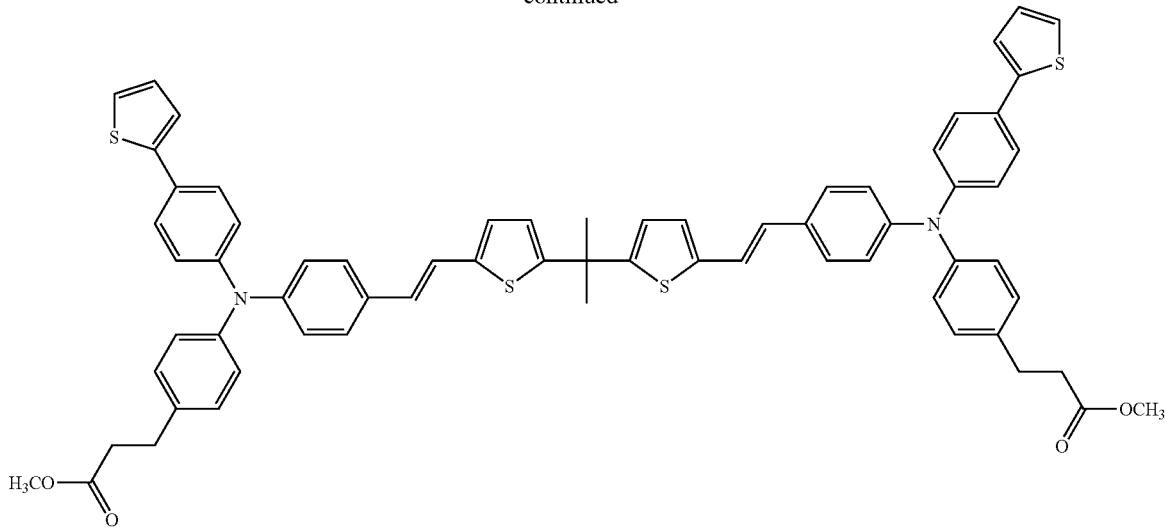

The present invention provides a thiophene-containing compound and a polymer thereof that are easily synthesized, are superior in solubility in solvents and resins and in film-forming property, and exhibit high mobility.

What is claimed is:

1. A thiophene-containing compound represented by Formula (I):

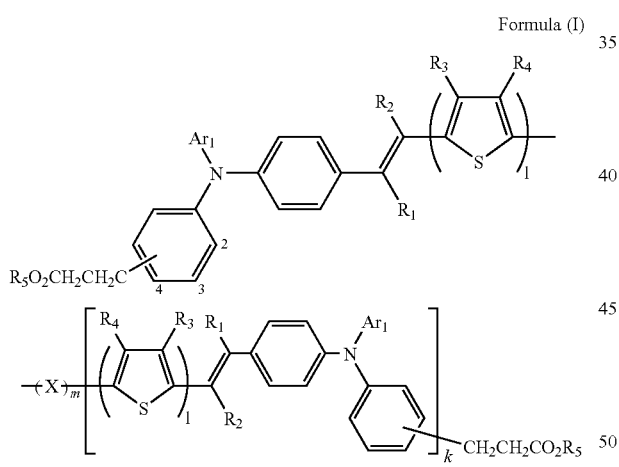

Formula (I)

wherein in Formula (I), $Ar_1$ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; $R_1$ to $R_5$ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

2. The thiophene-containing compound of claim 1, wherein in Formula (I), X represents a divalent straight-chain hydrocarbon group having 2 to 6 carbon atoms, a divalent branched-chain hydrocarbon group having 3 to 7 carbon atoms, a substituted or unsubstituted divalent polynuclear aromatic hydrocarbon having 1 to 8 aromatic rings, a substituted or unsubstituted divalent condensed aromatic hydrocarbon having 1 to 8 aromatic rings, or a substituted or unsubstituted divalent aromatic heterocyclic ring having 1 to 11 heterocyclic rings.

3. The thiophene-containing compound of claim 1, wherein in Formula (I), X represents a group represented by one selected from the group consisting of Structural Formulae (II-1) to (II-5):

Structural Formula (II-1)

Structural Formula (II-2)

Structural Formula (II-3)

Structural Formula (II-4)

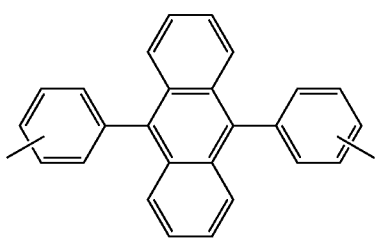

-continued

Structural Formula (II-5)

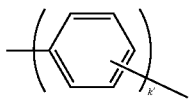

wherein in Structural Formula (II-1), $R_6$ represents a hydrogen atom, an alkyl group, a substituted or unsubstituted aryl group, or a substituted or unsubstituted aralkyl group; and in Structural Formula (II-5), k' represents an integer from 1 to 5.

4. The thiophene-containing compound of claim 1, wherein in Formula (I), $Ar_1$ represents a substituted or unsubstituted phenyl group.

5. The thiophene-containing compound of claim 1, wherein in Formula (I), $Ar_1$ represents a substituted or unsubstituted monovalent polynuclear aromatic hydrocarbon having 2 to 20 aromatic rings.

6. The thiophene-containing compound of claim 1, wherein in Formula (I), $Ar_1$ represents a substituted or unsubstituted monovalent condensed aromatic hydrocarbon having 2 to 20 aromatic rings.

7. The thiophene-containing compound of claim 1, wherein in Formula (I), $Ar_1$ represents a substituted or unsubstituted monovalent aromatic heterocyclic ring.

8. The thiophene-containing compound of claim 1, wherein in Formula (I), $Ar_1$ represents a substituted or unsubstituted monovalent aromatic group containing at least one aromatic heterocyclic ring.

9. A thiophene-containing compound polymer represented by Formula (III-1) or (III-2):

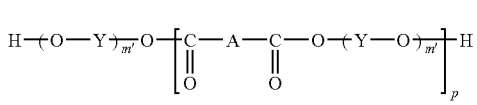

Formula (III-1)

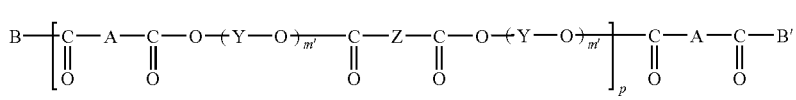

Formula (III-2)

wherein in Formulae (III-1) and (III-2), Y represents a divalent hydrocarbon group; Z represents a divalent hydrocarbon group; B and B' each independently represent —O—(Y—O)$_{m'}$—H or —O—(Y—O)$_{m'}$—CO-Z-CO-OR$_7$; $R_7$ represents a hydrogen atom, an alkyl group, a substituted or unsubstituted aryl group, a substituted or unsubstituted aralkyl group; m' represents an integer from 1 to 5; p represents an integer from 5 to 5,000; and A represents a group represented by Formula (IV),

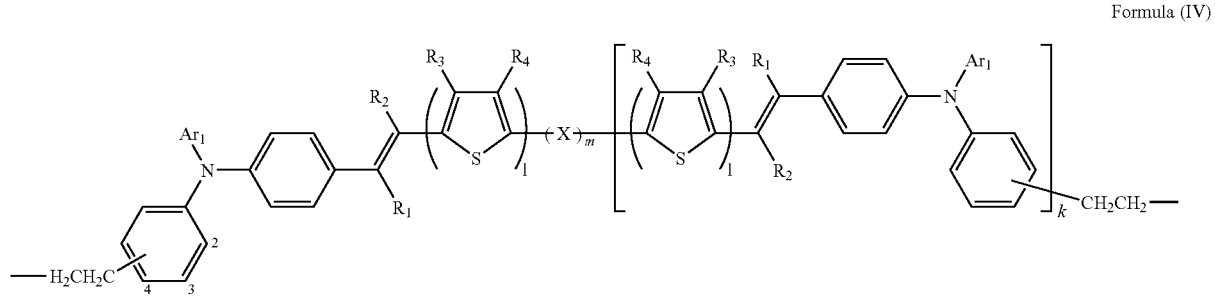

Formula (IV)

wherein in Formula (IV), Ar₁ represents a substituted or unsubstituted monovalent aromatic group; X represents a divalent straight-chain hydrocarbon group having 1 to 6 carbon atoms, a divalent branched-chain hydrocarbon group having 2 to 10 carbon atoms, or a substituted or unsubstituted divalent aromatic group; R₁ to R₄ each independently represent a hydrogen atom, an alkyl group, a cyano group, a halogen group, a substituted amino group, a substituted or unsubstituted aryl group, or a substituted or unsubstituted aralkyl group; l represents an integer from 1 to 5; and m and k each independently represent 0 or 1.

10. The thiophene-containing compound polymer of claim 9, wherein in Formula (IV), X represents a divalent straight-chain hydrocarbon group having 2 to 6 carbon atoms, a divalent branched-chain hydrocarbon group having 3 to 7 carbon atoms, a substituted or unsubstituted divalent polynuclear aromatic hydrocarbon having 1 to 8 aromatic rings, a substituted or unsubstituted divalent condensed aromatic hydrocarbon having 1 to 8 aromatic rings, or a substituted or unsubstituted divalent aromatic heterocyclic ring having 1 to 11 heterocyclic rings.

11. The thiophene-containing compound polymer of claim 9, wherein in Formula (IV), X represents a group represented by one selected from the group consisting of Structural Formulae (II-1) to (II-5):

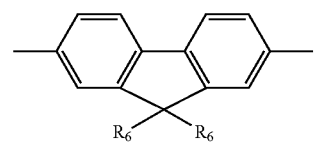

Structural Formula (II-1)

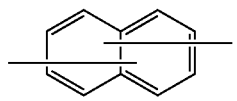

Structural Formula (II-2)

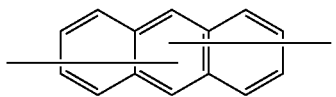

Structural Formula (II-3)

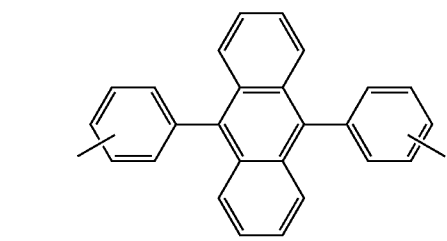

Structural Formula (II-4)

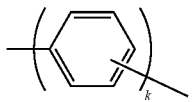

Structural Formula (II-5)

wherein in Structural Formula (II-1), R₆ represents a hydrogen atom, an alkyl group, a substituted or unsubstituted aryl group, or a substituted or unsubstituted aralkyl group; and in Structural Formula (II-5), k' represents an integer from 1 to 5.

12. The thiophene-containing compound polymer of claim 9, wherein in Formula (IV), Ar₁ represents a substituted or unsubstituted phenyl group.

13. The thiophene-containing compound polymer of claim 9, wherein in Formula (IV), Ar₁ represents a substituted or unsubstituted monovalent polynuclear aromatic hydrocarbon having 2 to 20 aromatic rings.

14. The thiophene-containing compound polymer of claim 9, wherein in Formula (IV), Ar₁ represents a substituted or unsubstituted monovalent condensed aromatic hydrocarbon having 2 to 20 aromatic rings.

15. The thiophene-containing compound polymer of claim 9, wherein in Formula (IV), Ar₁ represents a substituted or unsubstituted monovalent aromatic heterocyclic ring.

16. The thiophene-containing compound polymer of claim 9, wherein in Formula (IV), Ar₁ represents a substituted or unsubstituted monovalent aromatic group containing at least one aromatic heterocyclic ring.

17. The thiophene-containing compound polymer of claim 9, wherein in Formulae (III-1) and (III-2), p represents an integer from 10 to 1,000.

18. The thiophene-containing compound polymer of claim 9, wherein a weight-average molecular weight Mw of the polymer is in a range of 10,000 to 300,000.

* * * * *